(12) United States Patent
Soled et al.

(10) Patent No.: US 7,875,742 B2
(45) Date of Patent: Jan. 25, 2011

(54) HYDROGENATION PROCESSES

(75) Inventors: Stuart Leon Soled, Pittstown, NJ (US); Andrzej Malek, Baton Rouge, LA (US); James Clarke Vartuli, Schwenksville, PA (US); Jennifer Schaefer Feeley, Lebanon, NJ (US); Sabato Miseo, Pittstown, NJ (US); Shifang Luo, Pittsford, NY (US); Richard Henry Schlosberg, Bridgewater, NJ (US); Joseph Ernest Baumgartner, Califon, NJ (US); Christine E. Kliewer, Clinton, NJ (US); Steven T. Ragomo, Perkasie, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/712,793

(22) Filed: Feb. 25, 2010

(65) Prior Publication Data

US 2010/0184895 A1     Jul. 22, 2010

Related U.S. Application Data

(63) Continuation of application No. 10/534,075, filed as application No. PCT/EP03/12885 on Nov. 18, 2003, now Pat. No. 7,732,634.

(30) Foreign Application Priority Data

Nov. 20, 2002    (GB)   .................................. 0227086.6

(51) Int. Cl.
     *C07C 69/74*      (2006.01)
(52) U.S. Cl. ...................................... 560/127
(58) Field of Classification Search ................. 560/127; 562/509
See application file for complete search history.

(56) References Cited

U.S. PATENT DOCUMENTS 2,889,287 A     6/1959    Scott, Jr.

(Continued)

FOREIGN PATENT DOCUMENTS

EP      0 005 737      12/1979

(Continued)

OTHER PUBLICATIONS

Ahmen Kadry Aboul-Gheit: *The Role of Additives in the Impregnation of Platinum and Ruthenium on Alumina Catalysts*, Journal of Chemical Technology and Biotechnology, vol. 29, No. 8, Aug. 1979, pp. 480-486.

(Continued)

*Primary Examiner*—Taylor Victor Oh
(74) *Attorney, Agent, or Firm*—Andrew B. Griffis; Leandro Arechederra, III

(57) ABSTRACT

The present invention is directed to a process for hydrogenating one or more organic compounds especially unsaturated organic compounds by bringing the compound into contact with a hydrogen-containing gas in the presence of a catalyst, which comprises one or more catalytically active metals applied to a porous catalyst support. The one or more catalytically active metals having been derived via a decomposed organic complex of the metal on the support, in particular amine complexes of the metal. The decomposed complex may be treated with hydrogen to activate the catalyst before use as a hydrogenation catalyst.

22 Claims, 7 Drawing Sheets

U.S. PATENT DOCUMENTS

| | | | |
|---|---|---|---|
| 3,027,398 A | 9/1965 | Forsstrom et al. |
| 3,334,149 A | 8/1967 | Akin et al. |
| 3,761,428 A | 9/1973 | Sugler et al. |
| 4,073,750 A | 2/1978 | Yates et al. |
| 4,431,574 A | 2/1984 | Bournonville et al. |
| 5,098,684 A | 3/1992 | Kresge et al. |
| 5,102,643 A | 4/1992 | Kresge et al. |
| 5,250,282 A | 10/1993 | Kresge et al. |
| 5,286,898 A | 2/1994 | Gustafson et al. |
| 5,319,129 A | 6/1994 | Gustafson et al. |
| 5,837,639 A | 11/1998 | Kresge et al. |
| 5,936,126 A | 8/1999 | Ruhl et al. |
| 5,951,962 A | 9/1999 | Muller et al. |
| 6,238,701 B1 | 5/2001 | Muller et al. |
| 6,248,924 B1 | 6/2001 | Ruhl et al. |
| 6,284,917 B1 | 9/2001 | Brunner et al. |
| 2006/0149097 A1 | 7/2006 | Soled et al. |

FOREIGN PATENT DOCUMENTS

| | | |
|---|---|---|
| EP | 0 603 825 | 6/1994 |
| WO | WO 98/47618 | 10/1998 |
| WO | WO 99/32427 | 7/1999 |
| WO | WO 2004/046076 | 6/2004 |

OTHER PUBLICATIONS

Robert Schaffer: *Development of Clinical Reference Method for Glucose in Serum*, Pure & Application Chemical, 1976, vol. 45, p. 79.

P.A. Winsor: *Binary and Multicomponent Solutions of Amphiphilic Compounds, Solubilization and the Formation, Structure, and Theoretical Significance of Liquid Crystalline Solutions*, Winsor Chemical Reviews, 1969, vol. 68, No. 1.

U. Ciesla; F. Schuth: *Review of Ordered Mesoporous Material*, Microporous and Mesoporous Materials, 1999, vol. 27, pp. 131-149.

J. Lemaitre et al.: *The Measurement of Catalyst Dispersion*, pp. 299-365, 1984.

K. Nakamoto: *Infrared and Raman Spectra of Inorganic and Coordination Compounds*, Third Edition, 1978, Wehr Professor of Chemistry, Marquette University, pp. 267-269.

HYDROGENATION PROCESSES

CROSS REFERENCE TO RELATED APPLICATIONS

This application is a continuation of Ser. No. 10/534,075, filed Feb. 17, 2006, now U.S. Pat. No. 7,732,634, which is a national stage application of International Application No. PCT/EP03/12885, filed Nov. 18, 2003, which claims the benefit of GB 0227086.6, filed Nov. 20, 2002, the disclosures of which are herein incorporated by reference in their entireties.

FIELD OF THE INVENTION

The present invention relates to a process for the hydrogenation of organic compounds and to a process for the manufacture of a hydrogenation catalyst and in particular to a hydrogenation process that utilizes a hydrogenation catalyst prepared via the formation and decomposition of an organic complex on a catalyst support.

BACKGROUND OF THE INVENTION

Hydrogenation is an established process both in the chemical and petroleum refining industries. Hydrogenation is conventionally carried out in the presence of a catalyst, which usually comprises a metal hydrogenation component deposited on a porous support material. The metal hydrogenation component is often one or more metals for example nickel, platinum, palladium, rhodium, ruthenium or mixtures thereof.

Many organic compounds have one or more groups or functionality that is susceptible to hydrogenation under appropriate conditions with the use of a suitable metal containing catalyst. One particular group of compounds that are susceptible to hydrogenation is those that contain one or more unsaturated groups or functionality such as for example carbon-carbon double bonds or triple bonds.

Hydrogenated derivatives of benzenepolycarboxylic acids or derivatives thereof, such as esters and/or anhydrides, have many uses. Of particular interest is their use as plasticisers for polymeric materials. In this context the dialkylhexahydrophthalates are an example of one class of these compounds that are of particular interest. These materials may be produced by hydrogenation of the corresponding phthalic acid ester in the presence of hydrogen and an active metal hydrogenation catalyst deposited on a support.

In U.S. Pat. Nos. 5,286,898 and 5,319,129, dimethylterephthalate is hydrogenated at >140° C. and a pressure of from 50 to 170 bar over supported Pd catalysts, which are treated with Ni, Pt and/or Ru to give the corresponding dimethylhexahydroterephthalate. The supports used are alumina of crystalline phase alpha or theta or delta or gamma or beta or mixtures thereof.

In EP-A-0 005 737, aromatic carboxylic esters are hydrogenated at from 70 to 250° C. and from 30 to 200 bar over supported Ni, Ru, Rh and/or Pd catalysts to give the corresponding cycloaliphatic carboxylic esters. The support used is an aluminium oxide of which at least 20% has been converted into lithium-aluminium spinel.

U.S. Pat. No. 3,027,398 describes the hydrogenation of dimethylterephthalate over supported Ru catalysts at from 110 to 140° C. and from 35 to 105 bar. The Ru is deposited on charcoal or kieselguhr.

EP-A 0 603 825 relates to a process for the preparation of 1,4-cyclohexanedicarboxylic acid by hydrogenating terephthalic acid by using a supported palladium catalyst, wherein as support alumina, silica or active charcoal is used.

U.S. Pat. No. 3,334,149 describes a multistage process for the hydrogenation of dialkylterephthalate using a Pd catalyst followed by use of a copper chromite catalyst.

U.S. Pat. No. 5,936,126 describes a process for the hydrogenation of an aromatic compound. The catalyst used contains ruthenium as active metal alone or optionally with one or more other Group IB, VIIB or VIIIB metals on a macroporous support. The macroporous support exhibits an average pore diameter of at least 50 nm and a BET surface area of not more than about 30 $m^2/g$.

U.S. Pat. No. 6,248,924 describes a process for reacting organic compounds. The catalyst used contains ruthenium as active metal alone or optionally with one or more other Group IB, VIIB or VIIIB metals on a support. The support may be a material having macropores (50 to 10000 nm pore diameter) and mesopores (2 to 50 nm pore diameter). In the support 10-50% of the pores are macropores and 50 to 90% of the pores are mesopores. Alumina of surface area (BET) 238 $m^2/g$ is specifically exemplified.

Published International Application No. PCT/EP98/08346 (WO 99/32427) describes a process for the hydrogenation of benzene polycarboxylic acids or derivatives thereof. The catalyst used comprises ruthenium as an active metal which is deposited alone or together with at least one other metal of subgroups I, VII or VIII of the periodic table on a support. One of three separate types of support may be used. The first support is macroporous having a mean pore diameter of at least about 50 nm and a BET surface area of at most 30 $m^2/g$. The second support is a material, which has both macropores and mesopores (2 to 50 nm pore diameter), and in which 5-50% of the pores are macropores, 50 to 95% of the pores are mesopores and the surface area of the support is preferably from 50 to about 500 $m^2/g$. The third type of support is a material, which is macroporous and has a mean pore diameter of at least 50 nm and a surface area of at most 15 $m^2/g$.

Of particular importance in all hydrogenation processes is the degree of conversion of the starting materials and the selectivity of conversion into the desired hydrogenated products. The degree of conversion and selectivity should be as high as possible. In addition it is highly desirable to develop hydrogenation processes that proceed at acceptable reaction rates.

There is a need therefore for efficient hydrogenation processes for the hydrogenation of organic compounds and in particular for the hydrogenation of unsaturated compounds such as for example aromatic compounds to the corresponding ring-hydrogenated derivatives, which processes are highly selective and proceed at good reaction rates. It is therefore an object of the present invention to provide a process for hydrogenating organic compounds to hydrogenation products with high levels of conversion, selectivity and with good rates of reaction, and to provide a hydrogenation catalyst for use in such a hydrogenation process and to a process for the manufacture of such a hydrogenation catalyst.

SUMMARY OF THE INVENTION

The present invention accordingly provides a process for hydrogenating one or more organic compounds, which process comprises bringing the one or more organic compound into contact, under hydrogenation conditions, with a source of hydrogen in the presence of a catalyst comprising one or more catalytically active metal sites located on a catalyst support and recovering the hydrogenation products, wherein at least one of the catalytically active metal sites has been obtained via the decomposition on the support of an organic complex of the metal.

In a further aspect the present invention also provides a process for hydrogenating one or more benzenepolycarboxylic acids or one or more derivatives thereof, or a mixture of one or more benzenepolycarboxylic acids with one or more derivatives thereof by bringing, under hydrogenation conditions, the benzenepolycarboxylic acid or the derivative thereof or the mixture into contact with a hydrogen-containing gas in the presence of a catalyst, the catalyst comprising one or more catalytically active metal sites located on a catalyst support, wherein at least one of the catalytically active metal sites has been obtained via decomposition on the support of an organic complex of the metal.

In a further aspect the present invention also provides a process for the manufacture of a hydrogenation catalyst which process comprises;
 a) preparing a support having one or more organic complexes of one or more catalytically active metals located thereon; and
 b) decomposing one or more of the organic metal complexes located on the support.

In a further aspect the present invention also provides for a hydrogenation catalyst comprising one or more catalytically active metals and one or more support materials wherein the total metal dispersion is 45% or more and the metal dispersion relating to a strongly chemisorbed component of the total metal dispersion is 20% or greater.

In a further embodiment of each aspect of the present invention the organic complex on the support is partially decomposed.

In a further embodiment of each aspect of the present invention the organic complex on the support is fully decomposed.

In a further embodiment of each aspect of the present invention full decomposition may be achieved by exposing the organic complex on the support to pyrolysis conditions in the presence of hydrogen.

In a further embodiment of each aspect of the present invention the decomposition of the organic metal complex is followed by treatment of the fully or partially decomposed organic complex on the support with a source of hydrogen. When the hydrogen treatment is of a partially decomposed organic complex on the support the hydrogen treatment preferably fully decomposes the partially decomposed organic complex.

BRIEF DESCRIPTION OF THE DRAWINGS

The present invention will be better understood by reference to the Detailed Description of the Invention when taken together with the attached drawings wherein.

DETAILED DESCRIPTION OF THE INVENTION

Figure 1:
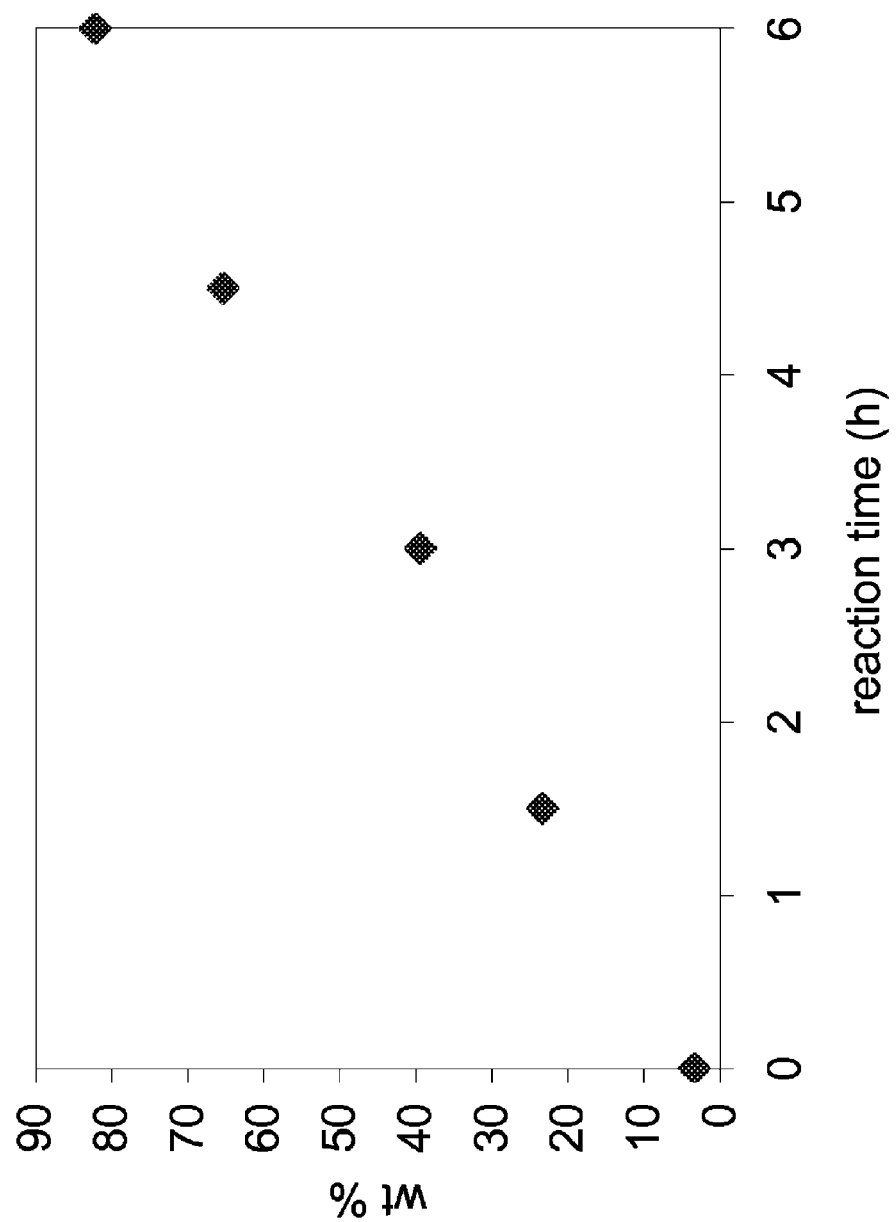
FIG. 1 shows a plot of DINP conversion vs reaction time for 0.5 wt % Ru/MCM-41 catalyst in which the active metal has been deposited from an aqueous solution.

In the process of the present invention organic compounds especially unsaturated organic compounds are hydrogenated in the presence of hydrogen and a hydrogenation catalyst that has been prepared in a specific way. The hydrogenation catalyst is prepared via the formation of one or more organic metal complexes, as the source of catalytically active metal. After deposition and/or formation of one or more organic metal complexes in or on the support material the complexes are partially or fully decomposed. This method of preparation results in hydrogenation catalysts that have good catalytic activity when compared to hydrogenation catalysts prepared using more conventional catalyst preparation methods. We have found that when at least one of the active hydrogenation metals is deposited in this way the resultant catalyst is highly active in hydrogenation processes. In a further embodiment the fully or partially decomposed organic complex is treated in a further stage with a source of hydrogen. This further stage may be omitted when a hydrogen source is used in a first stage to fully decompose the organic complex.

The process of the present invention is suitable for hydrogenating any organic compound that is susceptible to hydrogenation. Organic compounds that are particularly suitable are organic compounds that comprise one or more groups or functionality with unsaturated bonds; these compounds are herein described as "unsaturated organic compounds". The term "unsaturated organic compound" as used within the present invention comprises all organic compounds including low molecular weight (monomeric) and polymeric organic compounds which may be catalytically reacted, in particular those which exhibit groups which are treatable with hydrogen, such as carbon-carbon double or carbon-carbon triple bonds. This term comprises low molecular weight organic compounds as well as polymers. "Low molecular weight organic compounds" are compounds having a molecular weight of below 500. The term "polymer" is defined as relating to molecules having a molecular weight of higher than about 500.

In particular, organic compounds having one or more of the following structural units may be used, although the present invention is not limited to organic compounds that only have these structural units as groups that are susceptible to hydrogenation.

-continued

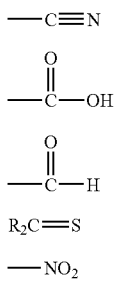

The process of the invention is particularly suitable for hydrogenating an unsaturated organic compound which is selected from the group consisting of an aromatic compound in which at least one hydroxyl group is bonded to an aromatic ring, an aromatic compound in which at least one amino group is bonded to an aromatic ring, an aromatic compound in which at least one carboxylic acid group or derivative thereof is bonded to an aromatic ring, a ketone, an aldehyde, a carboxylic acid or a derivative thereof, a polymer comprising at least one carbon-carbon double bond, a polymer comprising at least one carbonyl group, a polymer comprising at least one nitrile group, and a mixture of two or more thereof. Aliphatic unsaturated organic compounds comprising aldehyde groups as the only unsaturated group are not preferred. Aliphatic unsaturated organic compounds comprising aldehyde groups and alcohol groups especially polyols such as D-glucose are not preferred.

Within the process of the invention unsaturated organic compounds comprising units of different structures, as defined above, may be hydrogenated, such as unsaturated organic compounds, which exhibit carbon-carbon multiple bonds and carbonyl groups, since the catalyst used within the process of the invention are capable to first selectively hydrogenate one of the two groups, i.e. to achieve a hydrogenation of these groups from about 90 to 100%, while at first the other groups are reacted, preferably hydrogenated, to an extent of less than 25% and in general 0 to about 7%. Generally, first the carbon-carbon multiple bond and subsequently the nitrile group are reacted, e.g. hydrogenated, respectively.

The term "aromatic compound in which at least one hydroxyl group is bonded to an aromatic ring" or "aromatic compound in which at least one amino group is bonded to an aromatic ring" or "aromatic compound in which at least one carboxylic acid group or derivative thereof is bonded to an aromatic ring" means all compounds which have a unit of the structure (I):

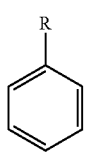

wherein R is a hydroxyl group or an amino group or carboxylic acid group or derivative thereof. In structure (I) there may be two or more substituent R groups in the aromatic ring.

If, in the process of the present invention, use is made of aromatic compounds in which at least one hydroxyl group and also at least one unsubstituted or substituted $C_1$-$C_{10}$-alkyl radical and/or $C_1$-$C_{10}$-alkoxy radical is bonded to an aromatic ring, the resulting isomer ratio of cis to trans products can be varied within a wide range, depending on the reaction conditions (temperature, solvent). Furthermore, the compounds obtained can be processed further without further purification steps, since the formation of alkylbenzenes is virtually completely avoided.

Like the above-described compounds in which at least one hydroxyl group is bonded to an aromatic ring, aromatic compounds in which at least one amino group is bonded to an aromatic ring can also be hydrogenated by the process of the present invention to give the corresponding cycloaliphatic compounds with high selectivity. For the amines additionally substituted by a $C_1$-$C_{10}$-alkyl radical and/or $C_1$-$C_{10}$-alkoxy radical, what has been said above regarding the ratio of the cis and trans isomers also applies.

In particular, this embodiment substantially avoids the formation of deamination products such as cyclohexanes or partially hydrogenated dimerization products such as phenylcyclohexylamines. In detail, the following compounds may be hydrogenated with the process of the invention.

Aromatic compounds in which at least one hydroxyl group and preferably also at least one unsubstituted or substituted $C_1$-$C_{10}$-alkyl radical and/or alkoxy radical is bonded to an aromatic ring can be hydrogenated by means of the process of the present invention to give the corresponding cycloaliphatic compounds, with it also being possible to use mixtures of two or more of these compounds. The aromatic compounds used can be monocyclic or polycyclic aromatic compounds. The aromatic compounds contain at least one hydroxyl group bonded to an aromatic ring; the simplest compound of this group is phenol. The aromatic compounds preferably have one hydroxyl group per aromatic ring and can be substituted on the aromatic ring or rings by one or more alkyl and/or alkoxy radicals, preferably $C_1$-$C_{10}$-alkyl and/or alkoxy radicals, particularly preferably $C_1$-$C_{10}$-alkyl radicals, in particular methyl, ethyl, propyl, isopropyl, butyl, isobutyl and tert-butyl radicals; among the alkoxy radicals, preference is given to $C_1$-$C_8$-alkoxy radicals such as the methoxy, ethoxy, propoxy, isopropoxy, butoxy, isobutoxy and tert-butoxy radicals. The aromatic ring or rings and also the alkyl and alkoxy radicals may be unsubstituted or substituted by halogen atoms, in particular fluorine atoms, or other suitable inert substituents.

Preferably, the compounds which can be hydrogenated according to the present invention have at least one, preferably from one to four, in particular one, $C_1$-$C_{10}$-alkyl radical which is preferably located on the same aromatic ring as the hydroxyl group or groups. Preferred compounds are (mono) alkylphenols, where the alkyl radical can be in the o, m or p position relative to the hydroxyl group. Particular preference is given to trans-alkylphenols, also known as 4-alkylphenols, where the alkyl radical preferably has from 1 to 10 carbon atoms and is, in particular, a tert-butyl radical. Preference is given to 4-tert-butylphenol. Polycyclic aromatic compounds, which can be used according to the present invention are, for example, β-naphthol and α-naphthol.

The aromatic compounds in which at least one hydroxyl group and preferably also at least one unsubstituted or substituted $C_1$-$C_{10}$-alkyl radical and/or alkoxy radical is bonded to an aromatic ring can also have a plurality of aromatic rings which are linked via an alkylene radical, preferably a methylene group. The alkylene group, preferably methylene group, which forms the linkage can have one or more alkyl substituents which can be $C_1$-$C_{20}$-alkyl radicals and are preferably $C_1$-$C_{10}$-alkyl radicals, particularly preferably methyl, ethyl, propyl, isopropyl, butyl or tert-butyl.

In these compounds, each of the aromatic rings can bear at least one bonded hydroxyl group. Examples of such compounds are bisphenols, which are linked in the 4 position via an alkylene radical, preferably a methylene radical.

In the process of the present invention, particular preference is given to reacting a phenol substituted by a $C_1$-$C_{10}$-alkyl radical, preferably $C_1$-$C_6$-alkyl radical, where the alkyl radical may be unsubstituted or substituted by an aromatic radical, or mixtures of two or more of these compounds. In a further preferred embodiment of this process, p-tert-butylphenol, bis(p-hydroxyphenyl)dimethylmethane or a mixture thereof is hydrogenated.

The process of the present invention also enables aromatic compounds in which at least one amino group is bonded to an aromatic ring to be hydrogenated to give the corresponding cycloaliphatic compounds, with mixtures of two or more of these compounds also being able to be used. The aromatic compounds can be monocyclic or polycyclic aromatic compounds. The aromatic compounds contain at least one amino group, which is bonded to an aromatic ring. The aromatic compounds are preferably aromatic amines or diamines and can be substituted on the aromatic ring or rings or on the amino group by one or more alkyl and/or alkoxy radicals, preferably $C_1$-$C_{20}$-alkyl radicals, in particular methyl, ethyl, propyl, isopropyl, butyl, isobutyl and tert-butyl radicals. Among the alkoxy radicals, preference is given to $C_1$-$C_8$-alkoxy radicals such as methoxy, ethoxy, propoxy, isopropoxy, butoxy, isobutoxy and tert-butoxy radicals. The aromatic ring or rings and also the alkyl and alkoxy radicals can be unsubstituted or substituted by halogen atoms, in particular fluorine atoms, or other suitable inert substituents.

The aromatic compound in which at least one amino group is bonded to an aromatic ring can also have a plurality of aromatic rings which are linked via an alkylene group, preferably a methylene group. The alkylene group, preferably methylene group, which forms the linkage can bear one or more alkyl substituents which can be $C_1$-$C_{20}$-alkyl radicals and are preferably $C_1$-$C_{10}$-alkyl radicals, particularly preferably methyl, ethyl, propyl, isopropyl, butyl, sec-butyl or tert-butyl.

The amino group bonded to the aromatic ring may be unsubstituted or substituted by one or two of the above-described alkyl radicals. Particularly preferred compounds are aniline, naphthylamine, diaminobenzenes, diaminotoluenes and bi-p-aminophenylmethane or mixtures thereof.

Within the process of the invention it is also possible to react, in particular to hydrogenate, compounds comprising carbonyl groups, i.e. in particular aldehydes, ketones, carboxylic acids and their derivatives, such as carboxylic acid esters, carboxylic acid halides and carboxylic anhydrides, and mixtures of two or more of the above-mentioned compounds.

In particular aldehydes and ketones, preferably those having 1 to 20 C-atoms, such as formaldehyde, acetaldehyde, propionaldehyde, n-butyraldehyde, valeraldehyde, caproaldehyde, heptaldehyde, phenylacetaldehyde, acrolein, crotonaldehyde, benzaldehyde, o-, m-, p-tolualdehyde, salicylic aldehyde, anisaldehyde, vanillin, zinnamic aldehyde, acetone, methyl ethyl ketone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, glycol aldehyde, glyoxal, 2,3-butandione, 2,4-pentandione, 2,5-hexandione, terephthalaldehyde, glutaraldehyde, diethylketone, methyl vinyl ketone, acetylacetone, 2-ethylhexanal, or mixtures of two or more thereof, may be used.

Furthermore, also polyketones, such as copolymers of ethylene and CO are used.

Furthermore, carboxylic acids and derivatives thereof, preferably those having 1 to 20 C-atoms may be reacted. In particular, the following are to be mentioned: Carboxylic acids, such as formic acid, acetic acid, propanoic acid, butanoic acid, iso-butanoic acid, n-valeric acid, pivalic acid, caproic acid, heptanoic acid, octanoic acid, decanoic acid, lauric acid, myristic acid, palmitic acid, stearic acid, acrylic acid, methacrylic acid, oleic acid, elaidic acid, linoleic acid, linolenic acid, cyclohexane carboxylic acid, benzoic acid, phenylacetic acid, o-, m-, p-toluoylic acid, o-, p-chlorobenzoic acid, o-, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid, trimellitic acid, trimesic acid, pyromellitic acid, hemimellitic acid and mixtures of two or more thereof.

Carboxylic acid halides, such as the chlorides and bromides of the above-mentioned carboxylic acids, in particular acetylchloride or -bromide, stearic acid chloride or -bromide and benzoic acid chloride or -bromide, which are dehalogenated.

Carboxylic acid esters, such as the $C_1$- to $C_{10}$-alkyl esters of the above-mentioned carboxylic acids, particularly methyl formate, acetic acid ester, butanoic acid butyl ester, dimethyl terephthalate, dimethyl adipate, methyl(meth)acrylate, butyrolactone, caprolactone and polycarboxylic acid esters, such as polyacrylic and polymethacrylic acid esters and copolymers and polyesters thereof, such as poly(methyl(meth)acrylates); these esters are in particular hydrogenated, i.e. the esters are reacted to the corresponding acids and alcohols.

Carboxylic anhydrides, such as anhydrides of the above-mentioned carboxylic acids, in particular acetic acid anhydride, propanoic acid anhydride, benzoic acid anhydride and maleic anhydride.

Carboxylic acid amides, such as amides of the above-mentioned carboxylic acids, such as formamide, acetamide, propionic amide, stearamide and terephthalamide.

In addition thereto, also hydroxy carboxylic acids, such as lactic, malic acid, tartaric acid or citric acid, or amino acids, such as glycine, alanine, proline and arginine may be reacted.

Furthermore, also nitriles, preferably aliphatic or aromatic mono or dinitriles, such as acetonitrile, propionitrile, butyronitrile, stearic acid nitrile, isocrotonic acid nitrile, 3-butylnitrile, 2,3-butadiene nitrile, 2,4-pentadiene nitrile, 3-hexene-1,6-dinitrile, chloracetonitrile, trichloracetonitrile, lactic acid nitrile, phenol acetonitrile, 2-chlorbenzonitrile, 2,6-dichlorobenzonitrile, isophthalonitrile, particularly aliphatic alpha, omega-dinitriles, such as succinonitrile, glutaronitrile, adiponitrile, pimelicnitrile and suberic nitrile or aminonitriles, such as 4-amino butanoic acid nitrile, 5-aminopentanoic acid nitrile, 6-aminohexanoic acid nitrile, 7-aminoheptanoic acid nitrile and 8-aminooctanoic acid nitrile.

Furthermore, within the process according to the invention, the following reactions may be carried out: The hydrogenation of aromatic compounds, such as benzene, toluenes, xylols, naphthalines and substituted derivatives thereof, leading to the corresponding alicyclic compounds; the hydrogenation of alkenes or alkynes, such as ethylene, propylene, 1-, 2-butene, 1-, 2-, 3- and 4-octene, butadiene, and hexatriene leading to the corresponding alkanes; the hydrogenation of nitroalkanes, such as nitroethane, nitromethane, nitropropane and 1,1-dinitroethane leading to the corresponding amines; the hydrogenation of imines, such as quinone imines, ketimines, ketene imines or aliphatic imines, such as propioamine, hexane imine; the dehalogenation or organic compounds which contain halogen atoms, particularly of aromatic halogen-containing compounds, such as chloro- and bromobenzene, bromo- and chlorotoluenes and chloro- and bromo xylols, also including compounds with more than one halogen atoms substituted, may be used; the aminating hydrogenation of i.e. alcohols, such as vinyl alcohol. Furthermore, within the process of the invention also oximes may be hydrogenated.

The catalysts according to the invention may be also used for the hydrogenation of large molecules, preferably of polymers. Accordingly, the present invention also relates to a process for hydrogenating a polymer comprising at least one catalytically reactable group in the presence of the above identified catalyst, wherein the hydrogenation of polymers comprising carbonyl groups, such as polyesters of dicarboxylic acids, unsaturated monocarboxylic acids, such as poly(meth)acrylates, olefin/CO-copolymers or polyketones, and the hydrogenation of polymers comprising nitrile groups, such as copolymers of styrene and butadiene, copolymers of acrylonitrile and the aminating hydrogenolysis of polyvinylalcohols and polyketones in the presence of the above-mentioned catalyst are preferred.

In particular, the present invention relates to a process for the hydrogenation of a polymer comprising at least one carbonyl group or a polymer comprising at least one nitrile group.

The term "polymer comprising at least one catalytically reactable group" relates to all polymers comprising such groups, in particular to polymers comprising units having the structures (I) to (VIII), as defined above with respect to the monomeric compounds, or a halogen atom. Needless to say that the referenced polymers comprise the respective unit at least once and that also one or more units of two or more of said structures may be present in the polymer reacted according to the invention.

The average molecular weight of the polymers to be reacted within the process of the invention is generally about 500 to about 500000, preferably about 1000 to about 100000 and more preferably about 1000 to about 50000. It is, however, possible to also react polymers having a higher molecular weight of up to one or several millions. If polymers comprising at least one carbon-carbon multiple bond, i.e. polymers comprising repeating units of the above defined structures (I) and (II) are reacted, these generally exhibit a weight average molecular weight of from about 5000 to about 1000000, preferably from about 50000 to about 500000 and more preferably from about 150000 to about 500000.

It is preferred to use polymers containing olefinic double bonds, and it is further preferred to use polymers containing diene units and copolymers containing vinylaromatic units and diene units. Within this reaction besides the catalyst comprising ruthenium as the active metal, also the catalyst comprising palladium as the active metal may be used. Common diene units include all conventional polyunsaturated monomers containing from three to twelve carbon atoms, butadiene being preferred. Copolymers to be hydrogenated may contain recurring units in random, block, or tapered distribution.

Aromatic monomers, which may be present in the polymers to be hydrogenated in the process of the invention, include monovinyl-substituted and polyvinyl-substituted aromatic compounds, the preferred monomers being styrene, alpha-methyl styrene, acrylonitrile, methacrylonitrile, and divinyl benzene. Furthermore, mixtures of vinylaromatic and/or diolefin monomers, optionally together with conventional olefinic monomers, can be present in the polymers to be hydrogenated.

As examples for polymers which may be hydrogenated with the process of the invention the following are to be mentioned: polymers having carbon-carbon double bonds, e.g. polybutadienes, such as poly(2,3-dimethylbutadiene), polyisoprene, polyacetylenes and polycylopenta- and -hexa-diene; polymers having carbon-carbon triple bonds, such as polydiacetylenes; polymers having aromatic groups, such as polystyrene, terpolymers of acrylonitrile, butadiene and styrene, and copolymers of styrene and acrylonitrile; polymers having carbon-nitrogen triple bonds, such as polyacrylonitrile, polyacrylonitrile-copolymers with e.g. vinyl chloride, vinylidene chloride, vinyl acetate or (meth)acrylic acid esters or mixtures of two or more thereof as comonomers; polymers having carbon-oxygen double bonds, such as polyesters, polyacrylamides, poly(acrylic acids), polyurea and polyketones; polymers having carbon-sulfur double bonds, such as polysulfones and polyethersulfones; halogen-containing polymers, such as poly(vinyl chloride) and poly(vinylidene chloride); and polymers containing nitro groups, which may be obtained by nitration of e.g. polyolefins by means of polymer analogous reactions.

Examples for polymers being preferably used within the present invention include polyisoprene, polybutadiene, ethylene/CO-copolymers, propylene/CO-copolymers, poly(m-ethyl(meth)acrylate), polyterephthalate, polyadipate, styrene-butadiene-copolymers, acrylonitrile-butadiene-copolymers, acrylonitrile-styrene-copolymers, styrene-isoprene-styrene-triblock copolymers, styrene-butadiene-styrene-triblock copolymers and styrene-butadiene-styrene-starblock copolymers.

Generally, a complete reaction of the introduced compounds is achieved. However, the reaction, preferably hydrogenation, may also be carried out in such a way that by suitably choice of temperature, $H_2$-pressure and/or $H_2$-amount only one of the type of groups susceptible to hydrogenation may be reacted, while the other kind of groups susceptible to hydrogenation are not appreciably hydrogenated.

The process of the invention is particularly suitable hydrogenating polymers comprising units of different structure, as defined above, e.g. a polymer comprising carbon-carbon multiple bonds and carbonyl groups and/or nitrile groups, since the catalyst of the present invention is capable to first selectively react the carbon-carbon multiple bond, e.g. to achieve a hydrogenation of these groups of about 90 to 100%, while at the same time the carbonyl groups and/or nitrile groups are reacted, e.g. hydrogenated to an extent of less than 25% and in general 0 to about 7%.

Furthermore, the process of the invention is particularly suitable for the hydrogenation of polymers of high molecular weight and containing both carbon-carbon multiple bonds and aromatic groups, since the catalysts used in the process of the invention are capable of achieving hydrogenation of the carbon-carbon multiple bonds, e.g. ethylenically unsaturated regions, to an extent of from 90 to 100%, whilst the aromatic regions are hydrogenated to an extent of less than 25% and generally to an extent of from 0% to 7%.

After finishing this reaction, preferably hydrogenation of the carbon-carbon multiple bonds, it is of course possible to nearly quantitatively react, preferably hydrogenate, the other unsaturated groups being present in the polymer, e.g. carbonyl groups by further introducing hydrogen. The process of the invention may be used for already isolated and living polymers.

The process of the present invention is of particular benefit in the hydrogenation of benzenepolycarboxylic acid or a derivative thereof, which are the most preferred organic compound for hydrogenation in the process. The term "benzenepolycarboxylic acid or a derivative thereof" used for the purposes of the present invention encompasses all benzenepolycarboxylic acids as such, e.g. phthalic acid, isophthalic acid, terephthalic acid, trimellitic acid, trimesic acid, hemimellitic acid and pyromellitic acid, and derivatives thereof, particularly monoesters, diesters and possibly triesters and tetraesters, in particular alkyl esters, and anhydrides such as phthalic anhydride and trimellitic anhydride or their esters. The esters used are alkyl, cycloalkyl and alkoxyalkyl esters, where the alkyl, cycloalkyl and alkoxyalkyl groups generally have from 1 to 30, preferably from 2 to 20 and particularly preferably from 3 to 18, carbon atoms and can be branched or linear.

One class of suitable benzenepolycarboxylic acids or a derivatives thereof are the alkyl terephthalates such as monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate and or dicyclohexyl terephthalate. Also suitable are derivates in which the alkyl groups of the ester groups are different alkyl groups. Mixtures of one or more alkyl terephthalates may be used.

Another suitable class are the alkyl phthalates such as monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, di-isoundecyl phthalate, diisododecyl phthalate, di-n-octadecyl phthalate, diisooctadecyl phthalate, di-n-eicosyl phthalate, monocyclohexyl phthalate, dicyclohexyl phthalate; alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate and or dicyclohexyl isophthalate. Also suitable are derivates in which the alkyl groups of the ester groups are different alkyl groups. Mixtures of one or more alkyl phthalates or isophthalates may be used.

A further suitable class are the alkyl trimellitates such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, diglycol esters of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, di-isoundecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and trimethyl trimellitate, triethyl trimellitate, tri-n-propyl trimellitate, tri-n-butyl trimellitate, tri-tert-butyl trimellitate, triisobutyl trimellitate, triglycol esters of trimellitic acid, tri-n-octyl trimellitate, triisooctyl trimellitate, tri-2-ethylhexyl trimellitate, tri-n-nonyl trimellitate, tri-isononyl trimellitate, tri-n-decyl trimellitate, triisododecyl trimellitate, tri-n-undecyl trimellitate, tri-isoundecyl trimellitate, triisododecyl trimellitate, tri-n-octadecyl trimellitate, triisooctadecyl trimellitate, tri-n-eicosyl trimellitate and tricyclohexyl trimellitate. Also suitable are derivates in which the alkyl groups of the ester groups are different alkyl groups. Mixtures of one or more alkyl trimellitates may be used.

Also suitable are the alkyl trimesates such as monomethyl trimesate, dimethyl trimesate, diethyl trimesate, di-n-propyl trimesate, di-n-butyl trimesate, di-tert-butyl trimesate, diisobutyl trimesate, monoglycol esters of trimesic acid, diglycol esters of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, di-isoundecyl trimesate, diisododecyl trimesate, di-n-octadecyl trimesate, diisooctadecyl trimesate, di-n-eicosyl trimesate, monocyclohexyl trimesate, dicyclohexyl trimesate, and also trimethyl trimesate, triethyl trimesate, tri-n-propyl trimesate, tri-n-butyl trimesate, tri-tert-butyl trimesate, triisobutyl trimesate, triglycol esters of trimesic acid, tri-n-octyl trimesate, triisooctyl trimesate, tri-2-ethyl-hexyl trimesate, tri-n-nonyl trimesate, tri-isononyl trimesate, tri-n-decyl trimesate, triisododecyl trimesate, tri-n-undecyl trimesate, tri-isoundecyl trimesate, triisododecyl trimesate, tri-n-octadecyl trimesate, triisooctadecyl trimesate, tri-n-eicosyl trimesate and tricyclohexyl trimesate. Also suitable are derivates in which the alkyl groups of the ester groups are different alkyl groups. Mixtures of one or more alkyl trimesates may be used.

A further suitable class are the alkyl hemimellitates such as monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, monoglycol esters of hemimellitic acid, diglycol esters of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hemimellitate, di-isoundecyl hemimellitate, diisododecyl hemimellitate, di-n-octadecyl hemimellitate, diisooctadecyl hemimellitate, di-n-eicosyl hemimellitate, monocyclohexyl hemimellitate, dicyclohexyl hemimellitate, and also trimethyl hemimellitate, triethyl hemimellitate, tri-n-propyl hemimellitate, tri-n-butyl hemimellitate, tri-tert-butyl hemimellitate, triisobutyl hemimellitate, triglycol esters of hemimellitic acid, tri-n-octyl hemimellitate, triisooctyl hemimellitate, tri-2-ethylhexyl hemimellitate, tri-n-nonyl hemimellitate, tri-isononyl hemimellitate, tri-n-decyl hemimellitate, triisodecyl hemimellitate, tri-n-undecyl hemimellitate, tri-isoundecyl hemimellitate, triisododecyl hemimellitate, tri-n-octadecyl hemimellitate, triisooctadecyl hemimellitate, tri-n-eicosyl hemimellitate and tricyclohexyl hemimellitate. Also suitable are derivates in which the alkyl groups of the ester groups are different alkyl groups. Mixtures of one or more alkyl hemimellitates may be used.

Another suitable class are the alkyl pyromellitates such as monomethyl pyromellitate, dimethylpyromellitate, diethyl pyromellitate, di-n-propyl pyromellitate, di-n-butyl pyromellitate, di-tert-butyl pyromellitate, diisobutyl pyromellitate, monoglycol esters of pyromellitic acid, diglycol esters of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, di-isoundecyl pyromellitate, diisodecyl pyromellitate, di-n-octadecyl pyromellitate, diisooctadecyl pyromellitate, di-n-eicosyl pyromellitate, monocyclohexyl pyromellitate, trimethylpyromellitate, triethyl pyromellitate, tri-n-propyl pyromellitate, tri-n-butyl pyromellitate, tri-tert-butyl pyromellitate, triisobutyl pyromellitate, triglycol esters of pyromellitic acid, tri-n-octyl pyromellitate, triisooctyl pyromellitate, tri-2-ethylhexyl pyromellitate, tri-n-nonyl pyromellitate, triisononyl pyromellitate, triisodecyl pyromellitate, tri-n-decyl pyromellitate, tri-n-undecyl pyromellitate, tri-isoundecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethylpyromellitate, tetraethyl pyromellitate, tetra-n-propyl pyromellitate, tetra-n-butyl pyromellitate, tetra-tert-butyl pyromellitate, tetraisobutyl pyromellitate, tetraglycol esters of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisodecyl pyromellitate, tetra-n-octadecyl pyromellitate, tetraisooctadecyl pyromellitate, tetra-n-eicosyl pyromellitate, tetracyclohexyl pyromellitate. Also suitable are derivates in which the alkyl groups of the ester groups are different alkyl groups. Mixtures of one or more alkyl pyromellitates may be used.

Also suitable are anhydrides of phthalic acid, trimellitic acid, hemimellitic acid and pyromellitic acid.

Also suitable are alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms (e.g. are $C_5$, $C_6$ or $C_7$ alkyl groups) such alkyl groups include; n-pentyl, 1-methylbutyl terephthalate, 2-methylbutyl, 3-methylbutyl, 2,2-dimethylpropyl, 1,1-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-methyl-2-ethylpropyl, 1-ethyl-2-methylpropyl, 1-ethylbutyl, 2-ethylbutyl, n-heptyl, 1-methylhexyl, 2-methylhexyl, 3-methylhexyl, 4-methylhexyl, 5-methylhexyl, 1,1-dimethylpentyl, 2,2-dimethylpentyl, 3,3-dimethylpentyl, 4,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1,3,3-trimethylbutyl, 2,3,3-trimethylbutyl, 1,2,3-trimethylbutyl, 1-ethyl-2-methylbutyl, 1-ethyl-3-methylbutyl, 2-ethyl-3-methylbutyl and 1-methyl-2-ethylbutyl. Also envisaged as suitable are compounds in which the alkyl groups are not identical such as for example in butylpropyl terephthalate or where one of the alkyl groups is replaced by a benzyl group such as for example in butylbenzyl terephthalate. Also suitable are mixtures of one or more alkyl terephthalates, alkyl phthalates, alkyl isophthalates, dialkyl or trialkyl trimellitates, dialkyl or trialkyl trimesates, dialkyl or trialkyl hemimellitates and dialkyl, trialkyl or tetraalkyl pyromellitates in which one or more of the alkyl groups contain 5, 6 or 7 carbon atoms.

In the process of the present invention it is also possible to use mixtures of one or more of the benzenepolycarboxylic acid or a derivative thereof described herein. When the derivatives are esters the mixture may be derived through use of a two or more alcohols in admixture or in sequence to esterify the same sample of a benzenepolycarboxylic acid derivative or a mixture of two or more benzenepolycarboxylic acids or a derivatives. Alternatively the alcohols may be used to form, in separate syntheses, two different esterified derivatives, which may then be mixed together to form a mixture of two or more esterified derivatives. In either approach the mixture may comprise a mixture of esters derived from branched or linear alcohols, for example the mixture may comprise ester derivatives prepared from C7, C9, C8, C10 and C11 linear or branched alcohols, preferably linear alcohols, with the alcohols being used in the same synthesis of a mixture of derivatives or in separate syntheses of the derivative where the resultant derivative products in each synthesis are combined to form a mixed derivative.

In the process of the present invention the preferred products are those derived from phthalates and in particular the following: cyclohexane-1,2-dicarboxylic acid di(isopentyl) ester, obtainable by hydrogenation of a di(isopentyl)phthalate having the Chemical Abstracts registry number (in the following: CAS No.) 84777-06-0; cyclohexane-1,2-dicarboxylic acid di(isoheptyl)ester, obtainable by hydrogenating the di(isoheptyl)phthalate having the CAS No. 71888-89-6; cyclohexane-1,2-dicarboxylic acid di(isononyl)ester, obtainable by hydrogenating the di(isononyl)phthalate having the CAS No. 68515-48-0; cyclohexane-1,2-dicarboxylic acid di(isononyl)ester, obtainable by hydrogenating the di(isononyl)phthalate having the CAS No. 28553-12-0, which is based on n-butene; cyclohexane-1,2-dicarboxylic acid di(isononyl)ester, obtainable by hydrogenating the di(isononyl)phthalate having the CAS No. 28553-12-0, which is based on isobutene; a 1,2-di-$C_9$-ester of cyclohexanedicarboxylic acid, obtainable by hydrogenating the di(nonyl)phthalate having the CAS No. 68515-46-8; cyclohexane-1,2-dicarboxylic acid di(isodecyl)ester, obtainable by hydrogenating a di(isodecyl)phthalate having the CAS No. 68515-49-1; 1,2-$C_{7-11}$-ester of cyclohexanedicarboxylic acid, obtainable by hydrogenating the corresponding phthalic acid ester having the CAS No. 68515-42-4; 1,2-di-$C_{7-11}$-ester of cyclohexanedicarboxylic acid, obtainable by hydrogenating the di-$C_{7-11}$-phthalates having the following CAS Nos.: 111381-89-6, 111381-90-9, 111381-91-0, 68515-44-6, 68515-45-7 and 3648-20-7; a 1,2-di-$C_{9-11}$-ester of cyclohexanedicarboxylic acid, obtainable by hydrogenating a di-$C_{9-11}$-phthalate having the CAS No. 98515-43-5; a 1,2-di (isodecyl)cyclohexanedicarboxylic acid ester, obtainable by hydrogenating a di(isodecyl)phthalate, consisting essentially of di-(2-propylheptyl)phthalate; 1,2-di-$C_{7-9}$-cyclohexanedicarboxylic acid ester, obtainable by hydrogenating the corresponding phthalic acid ester, which comprises branched and linear $C_{7-9}$-alkylester groups; respective phthalic acid esters which may be e.g. used as starting materials have the following CAS Nos.: di-$C_{7-9}$-alkylphthalate having the CAS No. 111 381-89-6; di-$C_7$-alkylphthalate having the CAS No. 68515-44-6; and di-$C_9$-alkylphthalate having the CAS No. 68515-45-7.

More preferably, the above explicitly mentioned $C_{5-7}$, $C_9$, $C_{10}$, $C_{7-11}$, $C_{9-11}$ and $C_{7-9}$ esters of 1,2-cyclohexanedicarboxylic acids are preferably the hydrogenation products of the commercially available benzenepolycarboxylic acid esters with the trade names Jayflex®DINP (CAS No. 68515-48-0), Jayflex® DIDP (CAS No. 68515-49-1), Jayflex® DIUP (CAS No. 85507-79-5), Jayflex® DTDP (CAS No. 68515-47-9), Palatinol® 911P, Vestinol® 9 (CAS No. 28553-12-0), TOTM-I® (CAS No. 3319-31-1), Linplast® 68-TM and Palatinol® N (CAS No. 28553-12-0) which are used as plasticizers in plastics.

Further examples of commercially available benzenepolycarboxylic acid esters suitable for use in the present invention include phthalates such as: Palatinol® AH (Di-(2-ethylhexyl)

phthalate; Palatinol® AH L (Di-(2-ethylhexyl)phthalate); Palatinol® C (Dibutyl phthalate); Palatinol® IC (Diisobutyl phthalate); Palatinol® N (Diisononyl phthalate); Palatinol® Z (Diisodecyl phthalate) Palatinol® 10-P (Di-(2-Propylheptyl)phthalate); Palatinol® 711P (Heptylundecyl phthalate); Palatinol® 911 (Nonylundecyl phthalate); Palatinol® 11P-E (Diundecyl phthalate); Palatinol® M (Dimethyl phthalate); Palatinol® A (Diethyl phthalate); Palatinol® A (R) (Diethyl phthalate); and Palatinol® K (Dibutylglycol phthalate). Further examples are the commercially available adipates such as: Plastomoll® DOA (Di-(2-ethylhexyl)adipate) and Plastomoll® DNA (Diisononyl adipate). Further examples of suitable commercially available materials are Vestinol® C (DBP), Vestinol® IB (DIBP), Vestinol® AH (DEHP), Witamol® 110 (610P) and Witamol® 118 (810P).

For the purposes of the present invention, the terms "macropores" and "mesopores" are used as they are defined in Pure Appl. Chem., 45 (1976), 79, namely as pores whose diameter is above 50 nm (macropores) or whose diameter is from 2 nm and 50 nm (mesopores).

The catalyst may be prepared using a wide variety of porous and non-porous support materials that are well known in the art. These include but are not limited to alumina, silica, $TiO_2$, $ZrO_2$, activated carbon, silicon carbide, magnesium oxide, zinc oxide and similar inorganic oxides or mixtures of two or more thereof. The preferred support materials are alumina, silica or mixtures thereof, with the most preferred material being silica, especially amorphous silica. In the process of the present invention the support is preferably a porous support. In one embodiment the support is preferably a support that comprises mesopores and most preferably as support that is substantially completely mesoporous or has as a major component, when the support is a mixture of two or more materials, at least one material that is substantially completely mesoporous. The preferred materials for use as supports in the present invention are amorphous materials such as alumina and silica with the most preferred support being amorphous silica. A further class of materials that may be used as supports in the present invention are crystalline materials such as crystalline molecular sieve materials and more preferably crystalline molecular sieve materials that are mesoporous. A further class of materials that may be use are ordered mesoporous materials.

Ordered mesoporous molecular sieve materials, which may be used as supports in the present invention, are those materials that may be synthesized using amphiphilic compounds as directing agents. Examples of such materials are described in U.S. Pat. No. 5,250,282, the whole contents of which are hereby incorporated by reference. Examples of amphiphilic compounds are also provided in Winsor, Chemical Reviews, 68(1), 1968. Other suitable ordered mesoporous materials of this type are also described in "Review of Ordered Mesoporous Materials", U. Ciesla and F. Schuth, Microporous and Mesoporous Materials, 27, (1999), 131-49. Such materials include but are not limited to materials designated as SBA (Santa Barbara) such as SBA-2, SBA-15 and SBA-16, materials designated as FSM (Folding Sheet Mechanism) such as FSM-16 and KSW-2, materials designated as MSU (Michigan State) such as MSU-S and MSU-X, materials designated as TMS or Transition Metal Sieves, materials designated as FMMS or functionalized monolayers on mesoporous supports and materials designated as APM or Acid Prepared Mesostructure. Particularly preferred ordered mesoporous materials are the silicate or aluminosilicate ordered mesoporous materials designated as M41S such as MCM-14, MCM-22, MCM-41, MCM-48, MCM-49, and MCM-50. These ordered mesoporous materials are described in detail in U.S. Pat. No. 5,102,643, the whole contents of which are hereby incorporated by reference. A particularly suitable sub-class of this family of materials for use in the present invention are the mesoporous silicas designated as MCM-41 and MCM-48. MCM-41 is particularly preferred and has a hexagonal arrangement of uniformly sized mesopores. MCM-41 molecular sieve materials are described in detail in U.S. Pat. No. 5,098,684, the whole contents of which are hereby incorporated by reference. The MCM-41 molecular sieves generally have a $SiO_2/Al_2O_3$ molar ratio when alumina is present and it is preferred that the $SiO_2/Al_2O_3$ molar ratio for these materials is greater than 100, preferably greater than 200, and most preferably greater than 300.

In one embodiment of the present invention, the hydrogenation process utilizes a catalyst, which comprises a hydrogenation function in the form of at least one active metal site on a support material comprising one or more ordered mesoporous materials with a unique structure and pore geometry as described below. These materials are inorganic, porous, non-layered materials which, in their calcined forms exhibit an X-ray diffraction pattern with at least one peak at a d-spacing greater than about 18 Angstrom Units (Å). They also have a benzene adsorption capacity of greater than 15 grams of benzene per 100 grams of the material at 50 torr and 25° C. In a preferred form, the support material is characterized by a substantially uniform hexagonal honeycomb microstructure with uniform pores having a cell diameter greater than 2 nm and typically in the range of 2 to 50 nm, more preferably 5 to 20 nm, and most preferably from 3 to 20 nm. Most prominent among these materials is a material identified as MCM-41, which is usually synthesized as a metallosilicate with Broensted acid sites by incorporating a tetrahedrally coordinated trivalent element such as Al, Ga, B, or Fe within the silicate framework. The preferred forms of these materials are the aluminosilicates although other metallosilicates may also be utilized. MCM-41 is characterized by a microstructure with a uniform, hexagonal arrangement of pores with diameters of at least about 2 nm: after calcination it exhibits an X-ray diffraction pattern with at least one d-spacing greater than about 18 Å and a hexagonal electron diffraction pattern that can be indexed with a $d_{100}$ value of greater than about 18 Å, which corresponds to the d-spacing of the peak in the X-ray diffraction pattern. This material is described below and in detail in Ser. No. 07/625,245, now U.S. Pat. No. 5,098,684 (Kresge et al) and U.S. Pat. No. 5,102,643 to Kresge et al., both of which are incorporated herein in their entirety.

The ordered mesoporous materials may be crystalline, that is having sufficient order to provide a diffraction pattern such as, for example, by X-ray, electron or neutron diffraction, following calcination, with at least one peak. These mesoporous materials may be characterized by their structure, which includes extremely large pore windows as well as high sorption capacities.

Ordered mesoporous materials as used in the present invention can be distinguished from other porous inorganic solids by the regularity of their large open pores, whose pore size more nearly resembles that of amorphous or paracrystalline materials, but whose regular arrangement and uniformity of size (pore size distribution within a single phase of, for example, +/−25%, usually +/−15% or less of the average pore size of that phase) resemble more those of crystalline framework materials such as zeolites. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as +/−25% random deviation from the average repeat distance between adjacent channels still clearly give recognizable images of the present ordered mesoporous materials.

The ordered mesoporous materials as used for preparation of the catalyst support preferably have the following composition:

$$M_{n/q}(W_aX_bY_cZ_dO_h)$$

wherein W is a divalent element, such as a divalent first row transition metal, e.g. manganese, cobalt and iron, and/or magnesium, preferably cobalt; X is a trivalent element, such as aluminium, boron, iron and/or gallium, preferably aluminium; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar 1 average valence of M; n/q is the number of moles or mole fraction of M; a, b, c, and d are mole fractions of W, X, Y and 1 Z, respectively; h is a number of from 1 to 2.5; and (a+b+c+d)=1. A preferred embodiment of the above crystalline material is when (a+b+c) is greater than d, and h=2. A further embodiment is when a and d=0, and h=2. In the as-synthesised form, the mesoporous material has a composition, on an anhydrous basis, expressed empirically as follows:

$$rM_{n/q}(W_aX_bY_cZ_dO_h)$$

wherein R is the total organic material not included in M as an ion, and r is the coefficient for R, i.e. the number of moles or mole fraction of R. The M and R components are associated with the material as a result of their presence during crystallisation, and are easily removed or, in the case of M, replaced by post-crystallisation methods hereinafter more particularly described.

To the extent desired, the original M, e.g. ammonium, sodium or chloride, ions of the as-synthesised material can be replaced in accordance with techniques well known in the art, at least in part, by ion exchange with other ions. Preferred replacing ions include metal ions, hydrogen ions, hydrogen precursor, e.g. ammonium, ions and mixtures thereof. Other M ions include rare earth metals and metals of Groups IA (e.g. K), IIA (e.g. Ca), VIIA (e.g. Mn), VIIIA (e.g. Ni), IB (e.g. Cu), IIB (e.g. Zn), IIIB (e.g. In), IVB (e.g. Sn), and VIIB (e.g. F) of the Periodic Table of the Elements (Sargent-Welch Co. Cat. No. S-18806, 1979) and mixtures thereof.

The preferred support for use in the present invention is a silica support. The preferred ordered mesoporous materials for use in the process of the present invention are the ordered mesoporous silicas. The most preferred ordered mesoporous silicas are those designated as M41S, with the most preferred being MCM-41.

Further examples of a mesoporous materials that may be used in the process of the present invention are the mesoporous silicas as described in and prepared according to U.S. Pat. No. 5,951,962, the disclosure of which is incorporated herein in its entirety. In this reference mesoporous silica is prepared by converting a silica precursor in a water and polymer dispersion containing reaction medium. The preferred polymer dispersion is a cationic polymer.

High surface area mesoporous alumina solids may be used in preparing the catalyst supports for use in the process of the present invention; such high surface area mesoporous alumina solids may be prepared according to the methods described in U.S. Pat. No. 6,238,701, the disclosure of which is incorporated herein in its entirety.

In one embodiment the support may be macroporous materials or materials that are both macroporous and mesoporous, such as those described in U.S. Pat. Nos. 5,936,126, 6,248,924 and 6,284,917 the disclosures of which are incorporated herein in their entirety.

Such macroporous materials have a mean pore diameter of at least about 50 nm, preferably at least about 100 nm, in particular at least about 500 nm. Preferably these macroporous materials have a BET surface area that is at most about 30 m$^2$/g, preferably at most about 15 m$^2$/g, more preferably at most about 10 m$^2$/g in particular at most about 5 m$^2$/g and more preferably at most about 3 m$^2$/g. The mean pore diameter of theses macroporous materials is preferably from about 100 nm to about 20000 nm, and more preferably from about 500 nm to about 5000 nm, and most preferably 500 nm to 1000 nm. The surface area of these macroporous materials is preferably from about 0.2 to about 15 m$^2$/g, more preferably from about 0.5 to about 10 m$^2$/g, in particular from about 0.5 to about 5 m$^2$/g and more preferably from about 0.5 to about 3 m$^2$/g. In this embodiment the pore size distribution of the macroporous material is preferably approximately bimodal, with the pore diameter distribution having one maxima at about 600 nm. Further preference is given to a macroporous material, which has a surface area of 1.75 m$^2$/g and this bimodal distribution of the pore diameter. The pore volume of the preferred macroporous material is preferably about 0.53 ml/g.

In a further embodiment the one or more materials of mixed porosity may be used in addition to a silica support and/or one or more materials having mesopores. These materials of mixed porosity may possess mesopores in addition to their macropores. Examples of such material are described in U.S. Pat. Nos. 6,248,924 and 6,284,917, the disclosures of which are incorporated herein in their entirety. In this embodiment the materials of mixed porosity may have a pore distribution in which from about 5 to about 50%, preferably from about 10 to about 45%, more preferably from about 10 to about 30% and in particular from about 15 to about 25%, of the pore volume is formed by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm where in each case the sum of the pore volumes adds up to 100%.

In this embodiment the total pore volume of the mixed porosity material is from about 0.05 to 1.5 cm$^3$/g, preferably from 0.1 to 1.2 cm$^3$/g and in particular from about 0.3 to 1.0 cm$^3$/g. The mean pore diameter of the mixed porosity material is preferably from about 5 to 20 nm, preferably from about 8 to about 15 nm and in particular from about 9 to about 12 nm.

The surface area of the mixed porosity material is preferably from about 50 to about 600 m$^2$/g, more preferably from about 200 to about 600 m$^2$/g and in particular from about 250 to about 600 m$^2$/g of the support.

The surface area of the macroporous materials and mixed porosity materials may be determined by the BET method using N$_2$ adsorption, in particular in accordance with DIN 66131. The mean pore diameter and the size distribution may be determined by Hg porosimetry, in particular in accordance with DIN 66133.

The macroporous materials and mixed porosity materials that may be used are, for example, macropore containing activated carbon, silicon carbide, aluminum oxide, silicon dioxide, titanium dioxide, zirconium dioxide, magnesium oxide, zinc oxide or mixtures of two or more thereof, with preference being given to using macropore containing alumina.

In one embodiment of the present invention the catalyst may consist solely of one or more active hydrogenation metals deposited on the surfaces of one or more supports such as amorphous silica or ordered mesoporous materials. In this embodiment the catalyst is free of added inorganic binder. The support with or without active metal deposited thereon may be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In a further embodiment the support material may be formed into composites with matrix materials resistant to the temperatures and other conditions employed in the hydrogenation process. Such materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. These materials may be incorporated into naturally occurring clays, e.g., bentonite and kaolin, to improve the crush strength of the catalyst under commercial operating conditions and function as binders or matrices for the catalyst. The catalyst support may be composited with the matrix material in amounts from 99:01 to 05:95 by weight, preferably from 99:01 to 10:90, more preferably from 99:01 to 20:80, and most preferably from 99:01 to 50:50 catalyst support:matrix material. Preferably, if used the additional matrix material is kept to a minimum typically less than 50 wt % of the combined weight of catalyst support and matrix material, ideally less than 40 wt %, preferably less than 30 wt %, more preferably less than 20 wt %, more preferably less than 15 wt %, most preferably less than 10 wt % and in a most preferred embodiment less than 5 wt %. Formation of the composition may be achieved by conventional means including mulling the materials together followed by extrusion of pelletizing into the desired finished catalyst particles. Ideally the additional matrix material is macroporous or is a material of mixed porosity i.e. both macroporous and mesoporous. The materials of mixed porosity may have a pore distribution in which from about 5 to about 50%, preferably from about 10 to about 45%, more preferably from about 10 to about 30 and in particular from about 15 to about 25%, of the pore volume is formed by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm where in each case the sum of the pore volumes adds up to 100%.

When used, the total pore volume of the mixed porosity material is from about 0.05 to 1.5 cm$^3$/g, preferably from 0.1 to 1.2 cm$^3$/g and in particular from about 0.3 to 1.0 cm$^3$/g. The mean pore diameter of the mixed porosity material is preferably from about 5 to 20 nm, preferably from about 8 to about 15 nm and in particular from about 9 to about 12 nm. The surface area of the mixed porosity material is preferably from about 50 to about 500 m$^2$/g, more preferably from about 200 to about 350 m$^2$/g and in particular from about 250 to about 300 m$^2$/g of the support.

The surface area of the macroporous materials and mixed porosity materials may be determined by the BET method using N$_2$ adsorption, in particular in accordance with DIN 66131. The mean pore diameter and the size distribution may be determined by Hg porosimetry, in particular in accordance with DIN 66133.

The macroporous materials and mixed porosity materials that may be used are, for example, macropore containing activated carbon, silicon carbide, aluminum oxide, silicon dioxide, titanium dioxide, zirconium dioxide, magnesium oxide, zinc oxide or mixtures of two or more thereof, with preference being given to using macropore containing alumina.

The catalyst used in the present invention comprises one or more active hydrogenation metals deposited on one or more support materials. The hydrogenation component is provided by a metal or combination of metals. Active metals that may be used are preferably one or more metals of transition group VIII of the Periodic Table. Preference is given to using platinum, rhodium, palladium, cobalt, nickel or ruthenium or a mixture of two or more thereof as active metal. A particular preference is given to using ruthenium, platinum, palladium nickel or mixtures of two or more thereof. A particularly preferred active metal is ruthenium or nickel, most preferably ruthenium. It has to be noted in this respect that besides one or more metals of transition group VIII metals other metals may used be used in combination with the group VIII metals such as Group IB, VIIB, or VIIIB metals.

The content of the metal component will vary according to its catalytic activity. Thus, the highly active noble metals may be used in smaller amounts than the less active base metals. For example, about 1 wt. percent or less or ruthenium, palladium or platinum will be effective. The metal component may exceed about 30 percent in a monolayer.

The active metal content is generally from about 0.01 to about 30% by weight, preferably from about 0.01 to about 5% by weight and in particular from about 0.1 to about 5% by weight, in each case based on the total weight of the catalyst used. A preferred catalyst is one that comprises ruthenium alone or in combination with one or more additional active metals at a total content of less than 5% by weight of active metal and preferably at a total content of less than 2% by weight of active metal. Preferably the content of ruthenium is from about 0.01 to 2%, more preferably 0.1 to 1% by weight of the total catalyst. When the support is used in combination with a matrix material it is preferred that the catalytically active metal sites are formed on the support before it is combined with the matrix material.

The hydrogenation catalyst is manufactured using a process according to the present invention in which a support is provided with one or more catalytically active metal sites through the use of a specific sequence of process steps. In the first step the support is provided with one or more organic complexes of one or more catalytically active metals in a second step the organic complex is either fully or partially decomposed.

In one embodiment a compound, or salt, of one or more catalytically active metals is combined with one or more organic compounds to form a mixture which is then contacted with a support to deposit the organic complex. In this embodiment the complex may be formed on formation of the mixture or may be formed after contact with the support and after removal of any solvent or solvents used during formation of the mixture. In another embodiment the support is first contacted with a compound, or salt, of one or more catalytically active metals followed by treatment with one or more organic compounds to form the organic complex on the support. In an alternative embodiment the support is first contacted with one or more organic compounds followed by treatment with a compound, or salt, or one or more catalytically active metals to form the complex on the support. In a further embodiment one or more organic compounds and a compound, or salt, or one or more catalytically active metals are contacted simultaneously with the support to form the organic complex. In yet a further embodiment a suitable organic complex of the desired metal may be synthesised and applied to the support via solution of the complex in a suitable solvent for the complex.

The one or more catalytically active metals may be exchanged onto the support material, impregnated into it or physically admixed with it. The application of the individual components or mixture of components may be achieved by steeping the support in an aqueous metal salt solution, or a solution in a suitable solvent of a compound of the metal, or in the mixture. The deposition may be achieved by dipping, spraying or any other method. Suitable metal salts for preparing the metal salt solutions are for example nitrates, nitrosyl nitrates, halides, carbonates, carboxylates, acetylacetonates, chloro complexes, nitrito complexes or ammine complexes of the corresponding metals, with preference being given to the nitrates and nitrosyl nitrates and most preferably the nitrosyl nitrates. When Pt is the active metal it is preferred that it is not complexed with the organic compound as its nitrate salt, preferably it is complexed as a chloride or hydroxide salt.

In the case of catalysts, which have a plurality of active metals applied to the support, the metal salts or metal salt solutions or metal compound solutions or mixtures may be applied simultaneously or in succession.

In the process of the present invention any organic compounds that are capable of forming organic complexes with the one or more catalytically active metals may be used. Typically these will be organic compounds that are capable of forming complexes that are stable under the conditions that are normally used for depositing catalytically active metals. Ideally, the organic compounds are selected to provide metal organic complexes that are stable under the conditions normally used for drying catalyst supports after impregnation with one or more catalytically active metals. Suitable organic compounds are well known in the art of transition metal chemistry and include such organic compounds as organic chelating agents, organic monodentate, bidentate and polydentate ligands commonly used in the preparation of transition metal coordination complexes. In a number of such complexes one or more ligands being covalently bonded molecules and/or ions may be present in the complex.

In the process of the present invention particularly suitable organic compounds are compounds that contain one or more amino groups such as amines or amino acids and most preferably organic compounds containing amino and alcohol groups.

The compounds containing one or more amino groups may be aliphatic amines, cycloaliphatic amines, aralkyl amines and alkylaryl amines. These may be primary, secondary and tertiary amines. They may also be quaternary ammonium salts with a counter ion. It is preferred that the nitrogen-containing compound is one or more primary, secondary or tertiary amines, preferably one or more aliphatic amines and most preferably one or more amines having one or more hydroxyl groups such as for example hydroxyalkylamines.

In one embodiment, the nitrogen-containing compound used according to the present invention has the following general formula:

$$NR^1R^2R^3 \qquad (I)$$

wherein $R^1$, $R^2$ and $R^3$ independently are one or more of the following groups: $C_1$-$C_{50}$-alkyl, $C_3$-$C_{50}$-cycloalkyl, aromatic, alkyl substituted aromatic, such as $C_1$-$C_{50}$-alkyl substituted aromatic, aromatic substituted aliphatic moieties such as $C_1$-$C_{50}$-alkylene moieties substituted with one or more aromatic groups, $C_1$-$C_{50}$-hydroxyalkyl, amino- and/or hydroxyl-substituted $C_1$-$C_{50}$-alkyl, alkoxyalkyl such as $C_2$-$C_{50}$-alkoxyalkyl, dialkylaminoalkyl such as $C_3$-$C_{50}$-dialkylaminoalkyl, alkylaminoalkyl such as $C_2$-$C_{50}$-alkylaminoalkyl, heterocyclic, aromatic heterocyclic, alkyl substituted heterocyclic and alkyl substituted aromatic heterocyclic, such as $C_1$-$C_{50}$-alkyl substituted heterocyclic and aromatic heterocyclic compounds, and heterocyclic substituted aliphatic moieties such as $C_1$-$C_{50}$-alkylene moieties substituted with one or more aromatic groups. In addition, $R^1$ and $R^2$ may independently be hydrogen. In another embodiment, $R^1$ and $R^2$ may form, with the nitrogen atom, a nitrogen-containing heterocycle, aromatic heterocycle, alkyl substituted heterocycle or alkyl substituted aromatic heterocycle.

Examples of alkyl groups include; methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably ethyl, isopropyl, 2-ethylhexyl, n-decyl, 2-n-propyl-n-heptyl, n-tridecyl, 2-n-butyl-n-nonyl and 3-n-butyl-n-nonyl, and $C_{40}$-$C_{200}$-alkyl such as polybutyl, polyisobutyl, polypropyl, polyisopropyl and polyethyl. The most preferred aliphatic amines are aliphatic amines having one or more alkyl groups having 1 to 20 carbon atoms and more preferably 2 to 14 carbon atoms.

Examples of cycloalkyl groups include $C_3$-$C_{12}$-cycloalkyl, preferably $C_3$-$C_8$-cycloalkyl such as cyclopropyl, cyclobutyl, cyclopentyl, cyclohexyl, cycloheptyl and cyclooctyl.

Examples of aromatic groups include; phenyl, 1-naphthyl, 2-naphthyl, 1-anthryl, 2-anthryl and 9-anthryl, 1-phenanthryl, 2-phenanthryl, 3-phenanthryl, 4-phenanthryl and 9-phenanthryl.

Examples of alkyl substituted aromatic groups include $C_7$-$C_{50}$ alkyl aromatic groups, preferably $C_7$-$C_{40}$-alkylphenyl such as 2-nonylphenyl, 3-nonlyphenyl, 4-nonylphenyl, 2-decylphenyl, 3-decylphenyl, 4-decylphenyl, 2,3-dinonylphenyl, 2,4-dinonylphenyl, 2,5-dinonylphenyl, 3,4-dinonylphenyl, 3,5-dinonylphenyl, 2,3-didecylphenyl, 2,4-didecylphenyl, 2,5-didecylphenyl, 3,4-didecylphenyl and 3,5-didecylphenyl, more preferably $C_7$-$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4, 6-trimethylphenyl, 2-ethylphenyl, 3-ethylphenyl, 4-ethylphenyl, 2-n-propylphenyl, 3-n-propylphenyl and 4-n-propylphenyl.

Examples of aromatic substituted aliphatic moieties include $C_7$-$C_{50}$ alkylene moieties substituted with one or more aromatic substituents, preferably $C_7$-$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl.

Examples of hydroxyalkyl groups include $C_1$-$C_{50}$-hydroxyalkyl, preferably $C_1$-$C_8$-hydroxyalkyl, particularly preferably $C_1$-$C_4$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxy-methyl-ethyl. Particularly preferred hydroxyalkyl group containing nitrogen compounds include the mono-, di-, and tri-, substituted aliphatic hydroxyalkylamines such as methanolamine, di-methanolamine, tri-methanolamine, ethanolamine, di-ethanolamine, tri-ethanolamine, butanolamine, di-butanolamine, tri-butanolamine, propanolamine, di-propanolamine, and tri-propanolamine.

Examples of amino- and hydroxyalkyl groups include $C_1$-$C_{50}$-alkyl, preferably amino- and/or hydroxyl-substituted $C_1$-$C_8$-alkyl, particularly preferably amino and/or hydroxyl-substituted $C_1$-$C_4$-alkyl such as N-(hydroxyethyl)aminoethyl and N-(amino ethyl)amino ethyl.

Examples of alkoxyalkyl groups include $C_2$-$C_{50}$-alkoxyalkyl, preferably $C_2$-$C_{20}$-alkoxyalkyl, particularly preferably $C_2$-$C_8$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$-$C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl.

Examples of dialkylamino groups include $C_3$-$C_{50}$-dialkylaminoalkyl, preferably $C_3$-$C_{20}$-dialkylaminoalkyl, particularly preferably $C_3$-$C_{10}$-dialkylaminoalkyl such as dimethylaminomethyl, dimethylaminoethyl, diethylaminoethyl, di-n-propylaminoethyl and diisopropylamino ethyl.

Examples of alkylaminoalkyl groups include $C_2$-$C_{50}$-alkylaminoalkyl, preferably $C_2$-$C_{20}$-alkylaminoalkyl, particularly preferably $C_2$-$C_8$-alkylaminoalkyl such as methylaminomethyl, methylaminoethyl, ethylaminomethyl, ethylaminoethyl and iso-propylamino ethyl.

Examples of aromatic heterocycles include 2-pyridinyl, 3-pyridinyl, 4-pyridinyl, pyrazinyl, 3-pyrrolyl, 2-imidazolyl, 2-furanyl and 3-furanyl. Examples of alkyl substituted aromatic heterocycles include $C_4$-$C_{50}$ mono-hetarylalkyl, such as 2-pyridylmethyl, 2-furanyl-methyl, 3-pyrrolylmethyl and 2-imidazolylmethyl, and $C_4$-$C_{50}$-alkylhetaryl such as 2-methyl-3-pyridinyl, 4,5-dimethyl-2-imidazolyl, 3-methyl-2-furanyl and 5-methyl-2-pyrazinyl.

Examples of alkylaminoalkyl groups include $C_2$-$C_{50}$-alkylaminoalkyl, preferably $C_2$-$C_{16}$-alkylaminoalkyl such as methylaminomethyl, methylaminoethyl, ethylaminomethyl, ethylaminoethyl and isopropylaminoethyl.

Examples of dialkylaminoalkyl groups include $C_3$-$C_{50}$-dialkylaminoalkyl, preferably $C_3$-$C_{16}$-dialkylaminoalkyl such as dimethylaminomethyl, dimethylaminoethyl, diethylaminoethyl, di-n-propylaminoethyl and diisopropylaminoethyl.

Examples of heterocyclic compounds, include pyridine, pyrrole, imidazole, oxazole, thiazole, pyrazole, 3-pyrroline, pyrrolidine, pyrimidine, and substituted examples of these heterocyclic compounds. Examples of organonitrile compounds include acrylonitrile, alkyl nitriles such as for example methyl nitrile, and ethyl nitrile.

Suitable amino acids include natural and synthetic amino acids. The natural amino acids include all isomers of the following: alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, a particularly preferred amino acid is L-arginine.

The organic compound may be used at any suitable level in relation to the amount of salt or compound of the catalytically active metal. Ideally it is used at an appropriate mole ratio to convert all of the salt or compound of the catalytically active metal to one or more organic complexes. This may be a molar ratio of 1:1 or higher depending on the capacity of the metal to complex with the organic compound, the capacity of the organic compound to complex with the metal and the presence of other complexing ligands such as monodentate ligands. However it is possible to use levels of organic compound which are insufficient to complex with all of the catalytically active metal; in these circumstances not all of the metal is converted to organic complex and the resulting catalyst may contain catalytically active metal sites that have been derived from complexed and non-complexed metal intermediates. Ideally, the mole ratio of organic compound to catalytically active metal is within the range of 0.1:1 to 40:1, preferably, 0.1:1 to 30:1, more preferably 0.2:1 to 25:1, even more preferably 0.25:1 to 10:1 or 0.5:1 to 10:1, more preferably 0.25:1 to 5:1, and most preferably 0.5:1 to 5:1.

When the complex is formed in a mixture before contact with the support the mixture is usually and preferably formed in combination with a solvent, which may be water or an organic solvent or a mixture of water and solvent. The amount of solvent used may vary within wide ranges but is typically sufficient to ensure that the mixture may be effectively contacted with the support so as to wet support and when the support is porous to allow penetration of the mixture into the porous support. Typically the salt or compound of one or more catalytically active metals and the organic compound(s) are used in amounts which depending on their form allow the required mole ratios indicated above to be achieved in the mixture. The remainder of the mixture comprises one or more solvents which may be present in an amount from 1 to 99 wt % of the weight of the total mixture, preferably 5 to 90 wt % of the weight of the total mixture, more preferably 5 to 80 wt % of the weight of the total mixture, even more preferably 10 to 70 wt % of the weight of the total mixture and most preferably 10 to 65 wt % of the weight of the total mixture.

After formation of the organic complex on the support the support may and preferably is dried to remove most of the solvent and/or water present during formation of the complex. Drying may be achieved under ambient conditions such as room temperature or this may be achieved at elevated temperatures, preferably drying is at a temperature from 100 to 150° C. Preferably, little or no decomposition of the organic complex occurs during the drying phase and drying merely results in the removal of non-complexed volatile materials.

The second step in the process of the present invention for the manufacture of a hydrogenation catalyst is the decomposition of the organic complex on the support, which may be partial or full decomposition at this stage. Although not wishing to be bound by any theory it is believed that this decomposition results in the formation in-situ of one or more precursors to the catalytically active metal sites. It is believed that it is, in part, the formation of these precursors and their treatment with hydrogen that ensures that the final catalyst exhibits a high degree of catalytic activity and has high levels of metal dispersion within the catalyst. The hydrogen may be used in a further step after full or partial decomposition or the full or partial decomposition may be undertaken in the presence of hydrogen under pyrolysis conditions. An important parameter in the activity of catalytically active metals is the form of the metal on the support and the level of dispersion of the metal on the support. The process of the present invention produces hydrogenation catalysts that comprise catalytically active metal particles that are relatively small and highly dispersed. In addition the level of dispersion is relatively stable.

Chemisorption measurements are commonly used to estimate the size of supported metal catalysts and metal surface area. The general method for measuring metal surface area by chemisorption is described in J. Lemaitre et al., "Characterization of Heterogenous Catalysts", edited by Francis Delanney, Marcel Dekker, New York (1984), pp. 310-324. The total metal surface area on the catalyst is preferably from 0.01 to 10 $m^2/g$, particularly preferably from 0.05 to 5 $m^2/g$ and more preferably from 0.05 to 3 $m^2/g$ of the catalyst. From chemisorption measurements, the % dispersion (% of metal atoms that populate the surface of the metal particles) can be estimated since a properly chosen titrant used in the chemisorption measurements adsorbs only on metal atoms populating the surface. Consequently higher dispersion values indicate smaller particles with more of the metal atoms populating the surface. For many hydrogenation reactions, activity correlates with dispersion. The preferred method for determining metal dispersion is by using hydrogen as the chemisorption probe molecule under high vacuum static conditions as follows. The sample is held at a temperature of 40° C. and an 8-point isotherm (with pressures between 80 and 400 torr) is obtained using $H_2$ as the chemisorption probe molecule. The linear portion of this isotherm is extrapolated to zero pressure to obtain the total quantity of hydrogen chemisorbed; this is the combined dispersion. The sample is then evacuated at 40° C. to remove any weakly adsorbed hydrogen and the titration repeated to determine what is referred to as weak adsorption isotherm. The linear portion of this weak adsorption isotherm is extrapolated to zero pressure to obtain the quantity of weakly chemisorbed hydrogen. Subtraction of these two values for combined dispersion and weak dispersion yields the strongly held chemisorbed quantity. Thus this method provides values for the total metal dispersion, the dispersion due to weakly chemisorbed hydrogen and dispersion due to strongly chemisorbed hydrogen. The value for the strongly chemisorbed hydrogen is an accurate indication of metal dispersion. In many prior art references the metal dispersion figures provided are based on the total chemisorbed probe and are not split into strong and weak components. In the present invention it is preferred that the hydrogenation catalysts used have dispersion values relating to the strongly chemisorbed component in excess of 20% more preferably in excess of 25% and most preferably in excess of 30%. In addition total dispersion values in excess of 45% preferably in excess of 50%, more preferably in excess of 55%, and most preferably in excess of 60% are achieved. Preferably 40% or more of the total metal dispersion relates to the strongly chemisorbed component, more preferably 45% or more and most preferably 50% or more.

In the second step of the process for preparing the hydrogenation catalyst the organic complex is decomposed at least partially or fully decomposed. In the context of the present invention "partial decompositions" means that the chemical composition of the organic complex is varied; this may be due to a change in the structure of the organic complex or may be due to the chemical destruction of part of or a component of the complex. When the destruction is partial the method of destruction is selected to ensure that the removal of non-metal chemical species associated with the complex is incomplete. When the destruction is complete the only significant element of the complex remaining would be the one or more catalytically active metals as oxides when destruction is carried out under oxidizing conditions or the reduced metal when the destruction is carried out in the presence of hydrogen. There may also be residues such as carbon residues formed from decomposition of the organic complex. The partial decomposition is due to variations in structure and/or composition that do not normally occur under the drying conditions typically used in catalyst preparation methods. The changes of structure and/or composition under the conditions of the second stage may be detected and monitored using various analytical techniques that are well known in the art such as infra-red spectroscopy, mass spectroscopy, thermogravimetric analysis, gas or liquid chromatography and spectroscopy.

A variety of methods may be used to induce partial or full destruction of the organic complex. These include chemical methods such as chemically induced hydrolysis or decomposition such as by the treatment with acid or base or ozone or similar chemical active materials. Other methods for inducing full or partial decomposition include thermal methods such as pyrolysis and/or calcination, both of which are the preferred methods with particular preference being given to calcination. A further method is treatment with steam. In one embodiment the pyrolysis may be carried out in the presence of hydrogen; in this embodiment any subsequent treatment with hydrogen may be omitted.

When calcination or pyrolysis is used as the method for full or partial decomposition of the organic complex the exact conditions used will depend on the nature of the complex and especially its thermal stability and decomposition profile under elevated temperature. By using thermogravimetric methods or mass spectroscopy linked with controlled thermal decomposition of the organic complex it is possible to determine at what temperature either under calcination conditions or pyrolysis conditions that initial decomposition and total decomposition of the organic complex occurs. This indicates the temperature range at which this partial decomposition stage should be undertaken or the minimum temperature that should be selected of full decomposition is required. Alternatively when analysed by infra-red transmission spectroscopy it may be determined at what point in the treatment that a certain functional group is either removed from or formed in the organic complex; the temperature at which this occurs if below the total decomposition temperature may be selected as the temperature for the partial decomposition or if above the total decomposition temperature may be selected as the temperature for full decomposition. In the case where amines are used as the organic compound the temperature below which significant quantities of nitrogen oxides are produced may be selected as the temperature for treatment to induce partial decomposition. For other organic compounds it may be the temperature at which CO or $CO_2$ are removed from the complex. In the case of amines and especially amines containing hydroxyl groups or amino acids as the organic compound it may be the formation of new vibration bands that appear in the infra-red spectra at between 2100-2200 $cm^{-1}$ and tentatively assignable to complex carbon nitrogen species such as nitriles and isonitriles being present in the partially decomposed organic complex. Another method that may be used is where TGA analysis shows total weight loss of the organic complex; temperatures below total weight loss may be selected for partial decomposition and temperatures at or above the temperature for total weight loss may be selected for full decomposition.

When calcination is used to partially or fully decompose the organic complex the calcination temperatures used are typically within the range of 200 to 1000° C., preferably from 250 to 600° C. The exact temperature used will depend on whether or not full or partial decomposition of the organic complex is desired and will depend on the nature of the organic complex. Factors that may affect the decomposition temperature of the organic metal complex include the nature of the metal and/or organic compound within the complex. Another factor may be the nature of the counter-ion present when the metal is introduced in the form of a salt. Preferably when partial decomposition is required the support with the organic complex deposited thereon is calcined at a temperature that is less than the temperature as determined by TGA in air, at which total weight loss of the organic complex occurs. Preferably it is between 200° C. and the temperature at which total weight loss of the organic complex occurs. Preferably when full decomposition is required the support with the organic complex deposited thereon is calcined at a temperature that is at or above the temperature, as determined by TGA, at which total weight loss of the organic complex occurs. Preferably it is between the temperature at which total weight loss of the organic complex occurs and 1000° C. Under calcination conditions oxygen is present either as a component of an otherwise inert diluent or as a consequence of calcination being undertaken in air. When pyrolysis is used the pyrolysis may be undertaken in an inert atmosphere free of oxygen or in a hydrogen atmosphere that may be and preferably is free of oxygen. When pyrolysis is used the organic complexes may decompose at higher temperatures than those observed under calcinations conditions. As with calcination the temperature, under pyrolysis conditions, for partial or full decomposition may be determined using a variety of methods of which TGA is preferred. Preferably when partial decomposition is required under pyrolysis conditions in an inert atmosphere or under hydrogen, the support with the organic complex deposited thereon is pyrolysed in an inert atmosphere or under hydrogen at a temperature that is less than the temperature as determined by TGA in an inert atmosphere or under hydrogen, at which total weight loss of the organic complex occurs. Preferably it is between 200° C. and the temperature at which total weight loss of the organic complex occurs under pyrolysis conditions in an inert atmosphere or under hydrogen. Preferably when full decomposition is required the supports with the organic complex deposited thereon are pyrolysed at a temperature that is at or above the temperature, as determined by TGA, at which total weight loss of the organic complex occurs under pyrolysis conditions in an inert atmosphere or under hydrogen. Preferably it is the between the temperature, under pyrolysis conditions in an inert atmosphere or under hydrogen, at which total weight loss of the organic complex occurs and 1000° C. Preferably the supports with the organic complex deposited thereon are pyrolysed in nitrogen or hydrogen at a temperature of less than 1000° C. The support comprising organic complex may be calcined or pyrolysed at the partial decomposition temperature for a period of time that is sufficient to ensure the partial decomposition of the organic complex occurs. Typically this will be for a period of at least 20 minutes, preferably at least 30, more preferably at least 45 mins and most preferably for 1 hour or more. Typically the period of time is 48 hours or less, preferably 24 hours or less and most preferably 12 hours or less. When full decomposition is required the support comprising organic complex may be calcined or pyrolysed at the full decomposition temperature for a period of time that is sufficient to ensure the full decomposition of the organic complex.

After the partial or full decomposition of the organic complex the support comprising the partially or fully decomposed complex may be treated with a source of hydrogen. This may be omitted when the initial decomposition is undertaken in the presence of hydrogen. In a preferred embodiment this treatment is undertaken using conditions and methods normally used for the activation of hydrogenation catalysts. These conditions and methods are selected to ensure that catalytically active metal is converted to the catalytically active form. In one embodiment the treatment with hydrogen is carried out by contacting the support comprising fully or partially decomposed complex with a gas stream comprising free hydrogen at from 30 to 600° C., preferably from 100 to 550° C., even more preferably from 200 to 500° C., and most preferably from 200 to 450° C. The gas stream preferably consists of from 50 to 100% by volume of $H_2$ and from 0 to 50% by volume of $N_2$. The treatment may be carried our under a continuous flow of hydrogen under atmospheric pressure or under static conditions at elevated pressures up to 100 bar, preferably 1 to 90 bar, more preferably 1 to 20 bar. The activation may be undertaken for a period of up to 48 hours, preferably no more than 36 hours, more preferably less than 24 hours, and most preferably from 30 mins to 12 hours.

In a preferred embodiment the support comprising fully or partially decomposed complex is exposed to hydrogen at atmospheric pressure and the temperature raised at a rate slower than 5° C. $\min^{-1}$, more preferably slower than 5° C. $\min^{-1}$ and most preferably slower than 2° C. $\min^{-1}$ or less to the treatment temperature where hydrogen treatment is continued for a further 1 to 10 hours, preferably 2 to 8 hours and most preferably 3 to 6 hours. When the organic complex has been partially decomposed the exact temperature and time are selected to ensure that under hydrogen treatment any residual partially decomposed organic complex is removed. Therefore the hydrogen treatment temperature is generally higher than the decomposition temperature of the organic complex and the especially the partially decomposed organic complex.

If a plurality of active metals are to be applied to the support and the application is carried out in succession, the various process stages of the present invention may be repeated in order to deposit each metal in sequence.

The total metal surface area on the catalyst is preferably from 0.01 to 10 $m^2/g$, particularly preferably from 0.05 to 5 $m^2/g$ and more preferably from 0.05 to 3 $m^2/g$ of the catalyst. The metal surface area may be measured by the chemisorption method as herein described.

In the hydrogenation process of the present invention the hydrogenation conditions are selected taking into account the nature of the organic compound to be hydrogenated. Generally the hydrogenation process is carried out at from about 50 to 250° C., preferably from about 70 to 220° C., most preferably 75 to 200° C., and more preferably at greater than 80° C. The most preferred temperature range is from 80 to 200° C. The pressures used here are generally above 10 bar, preferably from about 30 to about 300 bar, and most preferably greater than 50, preferably greater than 75 bar and more preferably from 50 to 220 bar, especially 75 to 220 bar.

The process of the present invention may be carried out either continuously or batchwise, with preference being given to carrying out the process continuously.

When the process is carried out continuously and the organic compound to be hydrogenated is a benzenepolycarboxylic acid or derivative thereof, the amount of the benzenepolycarboxylic acid or derivative thereof to be hydrogenated or of the mixture of two or more thereof is preferably from about 0.05 to about 3 kg per liter of catalyst per hour, more preferably from about 0.1 to about 2 kg per liter of catalyst per hour, most preferably from 0.2 to 1 Kg per liter of catalyst per hour.

As hydrogenation gases, it is possible to use any gases which comprise free hydrogen and do not contain harmful amounts of catalyst poisons such as CO, $CO_2$, COS, $H_{2S}$ and amines. For example, waste gases from a reformer can be used. Preference is given to using pure hydrogen as the hydrogenation gas.

The hydrogenation of the present invention can be carried out in the presence or absence of a solvent or diluent, i.e. it is not necessary to carry out the hydrogenation in solution.

However, preference is given to using a solvent or diluent. Solvents or diluents, which can be used, are any suitable solvent or diluent. The choice is not critical as long as the solvent or diluent used is able to form a homogeneous solution with the benzenepolycarboxylic acid or ester to be hydrogenated. For example, the solvents or diluents can also comprise water. Examples of suitable solvents or diluents include the following: straight-chain or cyclic ethers such as tetrahydrofuran or dioxane, and also aliphatic alcohols in which the alkyl radical preferably has from 1 to 10 carbon atoms, in particular from 3 to 6 carbon atoms. Examples of alcohols, which are preferably used, are i-propanol, n-butanol, i-butanol and n-hexanol. Mixtures of these or other solvents or diluents can likewise be used.

The amount of solvent or diluent used is not restricted in any particular way and can be selected freely depending on requirements. However, preference is given to amounts which lead to a 10-70% strength by weight solution of the benzenepolycarboxylic acid or ester to be hydrogenated.

In the process of the present invention it is also possible to use one or more derivates of benzenepolycarboxylic acids in the unpurified state that is in the presence of one or more starting materials for their manufacture such as for example alcohol in the case of ester derivatives. Also present may be traces of monoester derivatives, un-reacted acid such as phthalic acid, sodium monoester derivatives and sodium salts of the acids. In this aspect the benzenecarboxylic acid derivative is hydrogenated prior to purification and after hydrogenation is then sent to process finishing for stripping, drying and polishing filtration. In this aspect the benzenecarboxylic acid derivative may be an intermediate feed containing high levels of alcohol in the case of ester derivatives. There may be present 5 to 30% excess alcohol than that required to achieve complete esterification of the acid. In one embodiment there may be an intermediate feed containing 8 to 10 wt % isononyl alcohol in di-isononyl phthalate.

In the process of the present invention the desired products are one or more cyclohexyl materials derived from the hydrogenation of the corresponding benzenepolycarboxylic acid or derivatives thereof. Ideally the benzenepolycarboxylic acid or derivatives thereof are converted to the desired product with a high degree of selectivity and with the maximum conversion possible of the benzenepolycarboxylic acid or derivatives thereof. Hydrogenations of this type often result in undesirable by-products of relatively low molecular weight and low boiling point; these by-products are referred to as "lights". In the context of the present invention "lights" are defined as materials in the as hydrogenated reaction product that are eluted before the object cyclohexyl materials when the as hydrogenated reaction product is analyzed by Gas Liquid Chromatography. Details for one suitable method for determining the "lights" content of a product obtained by the process of the present invention is provided in the specific examples. When using the process of the present invention it is possible to obtain greater than 95% conversion of the starting material (one or more benzenepolycarboxylic acid or derivatives thereof), whilst at the same time producing less than 1.5% by weight based on the total weight of reaction product of "lights". In the process of the present invention the product obtained directly from the hydrogenation reaction ideally contains the object cyclohexyl derivative(s) in an amount that equates to 97 or greater mole % conversion of the starting material, preferably 98.5 or greater mole % conversion, more preferably 99 or greater mole % conversion, and most preferably 99.9 or greater mole % conversion. In the process of the present invention the product obtained directly from the hydrogenation reaction ideally contains 1.3% or less, preferably 1.0% or less, more preferably 0.75% or less, even more preferably 0.5% or less, and in the most preferable embodiment less than 0.3% by weight based on the total weight of the reaction product of "lights". When as hydrogenated products of this level of purity are obtained it may be possible to use these materials directly in certain applications without the need for further purification of the as hydrogenated product such as plasticisers for plastics products.

The process of the present invention is further illustrated by means of the following examples.

EXAMPLES

Example 1

Preparation of MCM-41

A sample of MCM-41 (40 Å) was prepared in accordance with the method described below, which corresponds to Example 21 of U.S. Pat. No. 5,837,639. The following mixture (parts by weight—pbw) was charged to an autoclave:

83.7 pbw Cetyltrimethylammonium (CTMA) hydroxide prepared by contacting a 29 wt. % N,N,N-trimethyl-1-hexadecylammonium chloride solution with a hydroxide-for-halide exchange resin, 1.7 pbw sodium aluminate, 41.1 pbw tetramethylammonium silicate (10% aqueous solution), and 10.5 pbw precipitated hydrated silica (HiSil).

The mixture was crystallized at 100° C. for 20 hours with stirring under autogeneous pressure. The resulting product was recovered by filtration and dried in air at ambient temperature. The product was then calcined at 540° C. for one hour in nitrogen, followed by six hours in air. The calcined product had a surface area of 1120 m²/g and the following equilibrium adsorption capacities in gram/100 grams:

| | |
|---|---|
| $H_2O$ | 10.8 |
| Cyclohexane | >50 |
| n-Hexane | >50 |
| Benzene | 67 |

The product was identified as MCM-41 with an X-ray diffraction pattern that included a very strong relative intensity line at 38.4+/−2.0 Å, and weak lines at 22.6+/−1.0, 20.0+/−1.0, and 15.2+/−Å.

Example 1b

Preparation of MCM-41

A sample of MCM-41 (40 Å) was prepared in accordance with the following method:

The following mixture (parts by weight—pbw) was charged to an autoclave:

26.8 pbw distilled water, 3.5 pbw Cetyltrimethylammonium (CTMA) chloride (29 wt. % aqueous solution), 4.55 pbw precipitated hydrated silica (Ultrasil PM), 1 pbw Tetramethylammonium hydroxide (25 wt. % aqueous).

The mixture was crystallized at 150° C. for 20 hours with stirring under autogeneous pressure. The resulting product was recovered by filtration and dried in air at ambient temperature. The product was then calcined at 540° C. for one hour in nitrogen, followed by six hours in air. The product was identified as MCM-41. The calcined product has a surface area of 903 m$^2$/g and a pore size (determined by nitrogen adsorption) of 3.8 nm.

The analyses are as follows:

| | |
|---|---|
| Silica | 96.8 wt. % |
| Alumina | 0.1018 wt. % |
| Sodium | 0.0300 wt. % |
| Carbon | 0.11 wt. % |

Sorption capacities were as follows:

| | |
|---|---|
| H$_2$O | 5.9 wt. % |
| Cyclohexane | 53.9 wt. % |
| n-Hexane | 44.1 wt. % |

Example 2a

Preparation of Hydrogenation Catalyst—Ruthenium and MCM-41—TEA/Aqueous Method

A solution was prepared by combining with stirring 16.6 grams of ruthenium (III) nitrosyl nitrate aqueous solution with 25.7 grams of triethanolamine and 25.7 grams of distilled water. This solution was added slowly to 25 grams of MCM-41 of Example 1b and dried overnight at 100° C. The catalyst was then calcined to 400° C. for three hours in flowing air. The ruthenium content was a nominal 0.5%.

Example 2b

Preparation of Hydrogenation Catalyst—Ruthenium and MCM-41 Aqueous Method

A solution was prepared by combining with stirring 16.6 grams of ruthenium (III) nitrosyl nitrate aqueous solution with 51.4 grams of distilled water. This solution was added slowly to 25 grams of MCM-41 of Example 1b and dried overnight at 100° C. The catalyst was then calcined to 400° C. for three hours in flowing air. The ruthenium content was a nominal 0.5%.

Example 3

Reduction of Metal Component of Hydrogenation Catalysts of Examples 2a and 2b

The catalysts prepared in Examples 2 and 3 were activated under two sets of conditions a) and b) as follows:
a) Catalyst particles (10/20 mesh) were loaded into a stainless-steel catalyst basket then installed in a 300 cm$^3$ autoclave. Metal reduction was conducted under a continuous atmospheric hydrogen flow of ~100 cm$^3$ min$^{-1}$ at 200° C. for 18 hours.
b) Catalyst particles (10/20 mesh) were loaded into a stainless-steel catalyst basket then installed in a 300 cm$^3$ autoclave. Metal reduction was conducted under a static hydrogen pressure of 1250 psig (approx 86 bar) at 200° C. for 14 hours.

Example 4

Hydrogenation of Di-isononyl phthalate (DINP)

After hydrogen activation the autoclave, containing activated catalyst, was cooled to room temperature and 137.4-194.5 g (0.28-0.46 mol) of liquid DINP (Jayflex DINP (CAS No. 68515-48-0). The autoclave was sealed, heated to hydrogenation temperature of 80 or 120° C., and pressurized with hydrogen to either a pressure of 840 psig (approx 58 bar) or 3000 psig (approx 207 bar). Hydrogenation was carried out for up to 7 hours. During hydrogenation samples were taken at regular intervals to analyze the conversion of DINP and assess the level of lights formation. Conversion of DINP was calculated directly based on the peak areas of residual aromatic proton resonance in 1H NMR spectra. The lights content of the sample was determined by Gas Liquid Chromatography using a DB-1 column (60 m×0.25 mm×0.25 μm), operated at 40-275° C. at a ramp rate of 10° C./min and holding at 275° C. for 35 minutes. The lights were determined as being all peaks, which eluted before 24.5 minutes. Components eluted thereafter were considered as Cyclohexanedicarboxylates products. The conversions and selectivities for the various hydrogenations are provided in Table 1.

The data in this table indicates that the catalysts prepared via impregnation with a triethanolamine/aqueous ruthenium mixture are more active hydrogenation catalysts compared with those prepared via aqueous ruthenium impregnation without the use of triethanolamine. The data also indicates that the catalysts prepared via impregnation with a triethanolamine/aqueous ruthenium mixture produce lower levels of lights at higher hydrogenation pressures.

Figure 2:
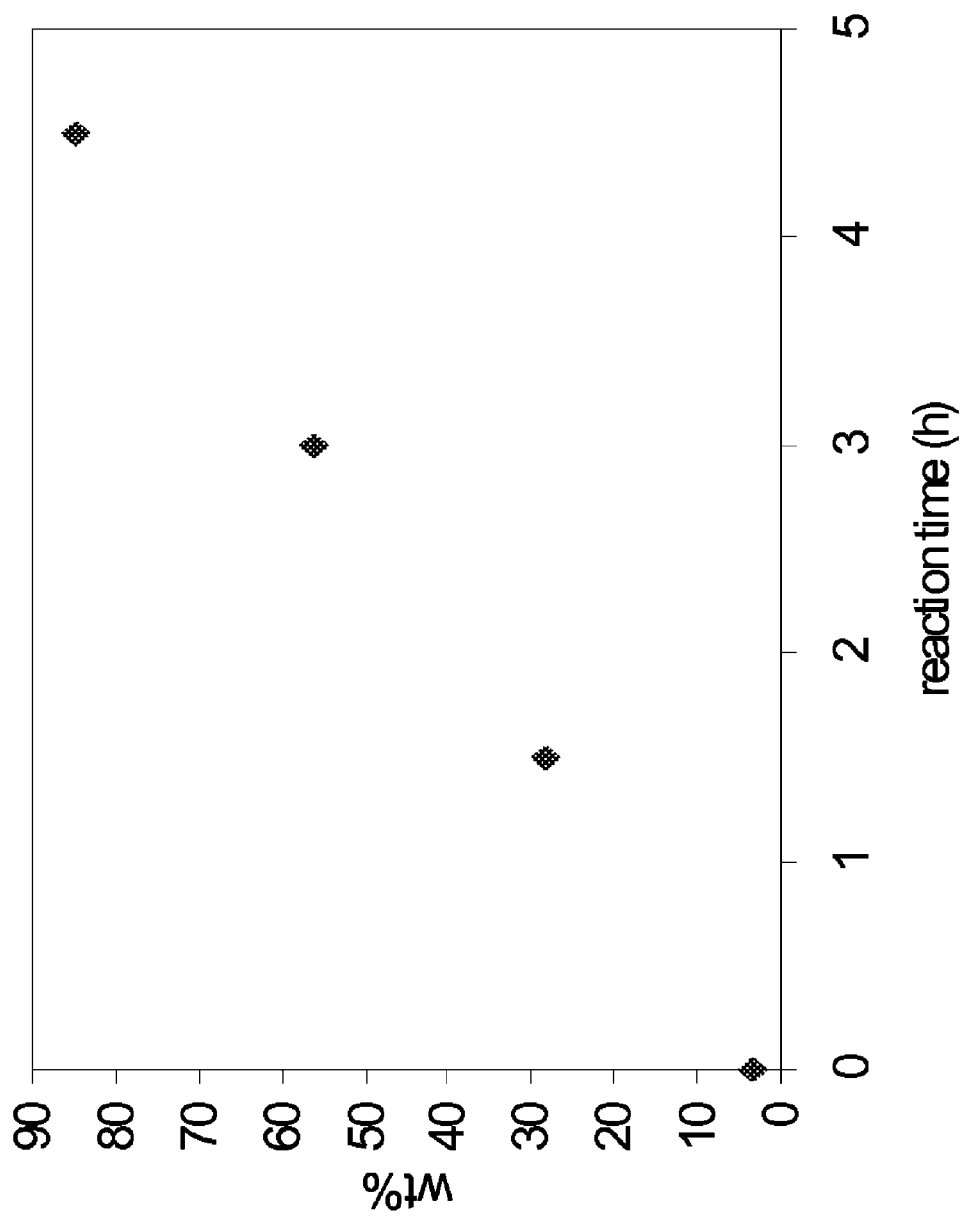
FIG. 2 shows a plot of DINP conversion vs reaction time for 0.5 wt % Ru/MCM-41 catalyst in which the active metal has been deposited from a mixture of an aqueous solution of metal with triethanolamine.

A comparison of FIG. 1 and FIG. 2 illustrates that the catalyst prepared according to the process of the present invention is significantly more active as a hydrogenation catalyst compared to the catalyst prepared via the conventional aqueous route. These plots of DINP conversion vs reaction time indicate that the DINP hydrogenation follows Langmuir-Hinshelwood kinetics Rate=$k$[DINP]/{1+$k'$[DINP]+$k''$[H6-DINP]}

To calculate the k value, only data with <90% DINP was used. At <90 DINP conversion and under constant H$_2$ pressure, DINP conversion is zero-order with respect to DINP concentration. The calculated k values for Examples 4 (d) and 4 (e) are 0.41 mole/litre·h and 0.31 mole/litre·h. Thus the catalyst prepared according to the process of the present invention is 32% more active than a catalyst prepared through aqueous impregnation.

Example 5

Hydrogen Treatment and Measurement of H Chemisorption Values for Supported Ru Hydrogenation Catalysts of Examples 6 to 14

(A) Activation. Approximately 0.3 to 0.5 grams of catalyst was loaded in the chemisorption cell, reduced in flowing hydrogen at one atmosphere total pressure at the temperature indicated in Tables 2 to 6. The samples were heated to the final reduction temperature at 2° C./min and held at this temperature for three hours. After this treatment the catalyst was activated and ready for use as a hydrogenation catalyst.

(B) The chemisorption measurements were obtained under static high vacuum conditions. After the hydrogen treatment under (A) hydrogen was then pumped off under dynamic vacuum for 15-30 minutes at the reduction temperature indicated in Tables 2 to 6. The temperature was lowered to 40° C. and an 8-point isotherm (with pressures between 80 and 400 torr) was obtained using $H_2$ as the chemisorption probe molecule. The linear portion of this isotherm was extrapolated to zero pressure to obtain the total quantity of hydrogen chemisorbed. This is shown in Tables 2 to 6 in the column labeled % dispersion (combined). The sample was evacuated at 40° C. to remove any weakly adsorbed hydrogen and the titration repeated to determine the weak adsorption isotherm. The linear portion of this isotherm was extrapolated to zero pressure to obtain the quantity of weakly chemisorbed hydrogen. This is shown in Tables 2 to 6 as the column labeled % dispersion (weak). Subtraction of these two values yields the strongly held chemisorbed quantity and is shown in accompanying tables below in the column labeled % dispersion (strong). All values are based on a $H/Ru_{surface}$ ratio of 1.

Example 6

Preparation of Organic Complex Comprising 0.5% Ru on $SiO_2$ Using Aminoalcohol in Impregnation Solution 15.00 g of silica support (S.A=85 $m^2$/g, P.D.=50 nm) was impregnated with solution prepared by mixing 5.01 g of ruthenium nitrosyl nitrate (1.5% Ru), 2.23 g triethanolamine and 1.77 g water and dried at 100° C. for four hours.

Example 7

Calcination of Catalyst of Example 6 to 300° C.

A portion of sample from Example 6 was calcined in flowing air as the temperature was ramped 1° C./minute to 300° C. and held for one hour at that temperature. A chemisorption measurement was made on this sample after hydrogen treatment.

Example 8

Calcination of Catalyst of Example 6 to 400° C.

A portion of sample from Example 6 was further calcined in air at a heating rate of 1° C./min to 400° C. and held at that temperature for 3 hours. A chemisorption measurement was made on this sample after hydrogen treatment.

Table 2 compares the dispersion measurements by H chemisorption of the catalysts of Examples 7 and 8. This comparison shows that the highest dispersions are obtained when the Ru-TEA on silica catalyst is calcined at 300° C., which partially decomposes the complex. After 400° C. calcination the organic complex is totally destroyed before hydrogen treatment and it can be seen that the chemisorption values are substantially lower and are unstable as they decrease as the reduction temperature is increased above 250° C. The higher values in the Example 7 catalyst remain stable during reduction at 400° C.

Example 9

Preparation of 0.5% Ru on $SiO_2$ Using Aminoalcohol in Impregnation Solution 25.00 g of silica support (S.A=250 $m^2$/g, P.D.=15 nm) was impregnated with solution prepared by mixing 8.37 g of ruthenium nitrosyl nitrate (1.5% Ru), 3.71 g triethanolamine and 18.00 g water and dried at 100° C. for four hours.

Example 10

Calcination of Catalyst of Example 9 to 275° C.

A portion of sample from Example 9 was calcined in flowing air as the temperature was ramped 1° C./minute to 275° C. and held at that temperature for one hour. A chemisorption measurement was made on this sample after hydrogen treatment.

Example 11

Pyrolyzing Catalyst of Example 9 in Oxygen-Free Environment

A portion of Sample from Example 9 was heated in flowing nitrogen as the temperature was ramped 2° C./minute to 400° C. and held at that temperature for one hour. A chemisorption measurement was made on this sample after hydrogen treatment.

Table 3 compares the dispersion measurements by H chemisorption of the catalysts of Examples 10 and 11. Both treatments generate a remnant of the starting Ru-triethanolamine complex. This comparison shows that the partial decomposition may be achieved at higher temperatures when under inert pyrolysis conditions (absence of oxygen) to form the Ru-organic precursor that gives high dispersion as well as when produced via oxidation.

Example 12

Comparative Sample of 0.5% Ru on Silica with No Organic Additive 15.00 g of silica support (S.A=85 $m^2$/g, P.D.=50 nm) was impregnated with solution prepared by mixing 5.00 g of ruthenium nitrosyl nitrate (1.5% Ru) and 4.00 g water and dried at 100° C. for four hours. A chemisorption measurement was made on this sample after hydrogen treatment.

Example 13

Comparative Sample of 0.5% Ru on Silica with No Organic Additive and Calcination 15.00 g of silica support (S.A=85 $m^2$/g, P.D.=50 nm) was impregnated with solution prepared by mixing 5.00 g of ruthenium nitrosyl nitrate (1.5% Ru) and 4.00 g water and dried at 100° C. for four hours. The sample was then calcined in air as the temperature was ramped 1° C./minute to 300° C. and held at that temperature for one hour. A chemisorption measurement was made on this sample after hydrogen treatment.

Table 4 compares the dispersion measurements by H chemisorption of the catalysts of Examples 7, 12 and 13. Only the catalyst prepared according to Example 7 in the Table is an object of this invention and has the remnant of the starting Ru-triethanolamine complex. This comparison shows that a high initial dispersion can be obtained on a catalyst that is simply impregnated with an aqueous solution of the Ruthenium salt and then dried at low temperature if it is reduced at temperatures as low as 150° C. On reduction at higher temperatures the dispersion numbers decrease dramatically, most probably as a result of sintering. This does not happen with the catalyst of Example 7, which remains stable at 400° C. reduction temperatures. If the aqueous salt solution of Ru is calcined first to 300° C. the dispersion numbers are very low (Example 13).

Example 14

Preparation of 0.5% Ru on $SiO_2$ Using Aminoacid in Impregnation Solution 10.00 g of silica support (S.A=85 $m^2$/g, P.D.=50 nm) was impregnated with solution prepared by mixing 3.34 g of ruthenium nitrosyl nitrate (1.5% Ru), 0.70 g L-arginine, and enough water to form a total 10 cc solution volume. The sample was dried at 100° C. for four hours and the temperature was then ramped 1° C./minute to 250° C. and held at that temperature for one hour. A chemisorption measurement was made on this sample after hydrogen treatment.

Table 5 compares the dispersion measurements by H chemisorption of the catalysts of Examples 7 and 14. Both calcined samples leave a remnant of the starting Ru-amino complexes. This comparison shows that high dispersions are obtained when using either aminoalcohols or aminoacids in the impregnation solution.

The data Table 6 shows the chemisorption data for Examples 9 and 10. This comparison shows that the dried catalyst with the amino complex (Example 9) gives a good dispersion value if directly reduced in hydrogen that is superior to the sample where the complex is completely oxidized to remove the complex (Example 8 see Table 2). However, the dispersion is not as good as that obtained if the organic complex is either partially oxidized or pyrolysed.

Example 16

Figure 3:
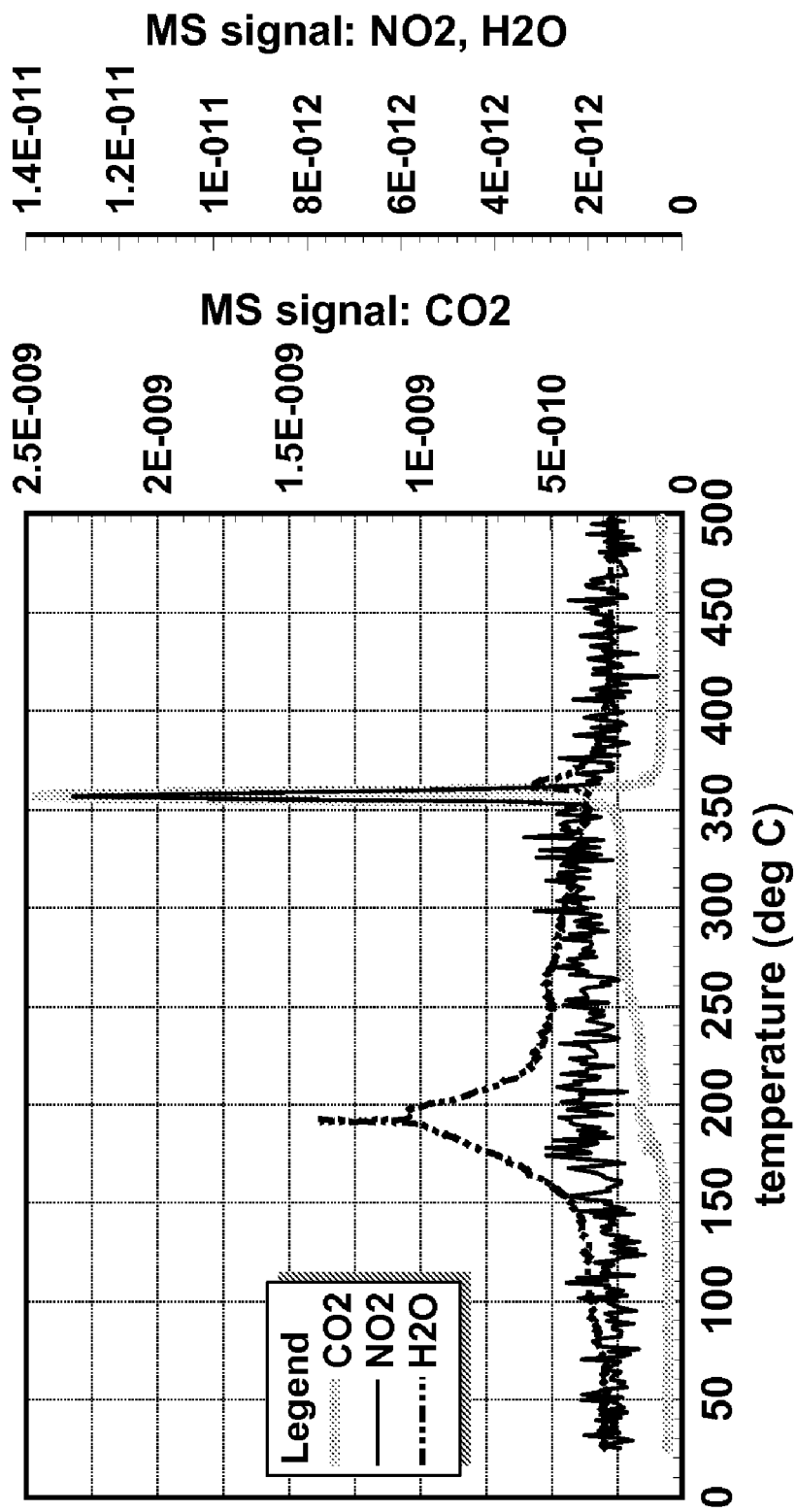
FIG. 3 shows a quadrapole mass spectrum of the product of Example 7 heated in air at 4 deg/min.

Measurement of Decomposition Products of Catalyst Precursor Formed by Partial Oxidation of Ru-Triethanolamine Complex A portion of the catalyst from Example 7 was heated in air at 4 deg/min and the product gas was analyzed by a quadrapole mass spectrometer. The data is shown in FIG. 3. FIG. 3 shows that a water peak is released slightly below 200° C. and then there is formation of $CO_2$, $NO_2$ and $H_2O$ as the organic complex is completely oxidized near to 350° C. This shows that the complex contained C, N and H. There might be O as well but we cannot tell from this experiment as it is carried out under oxidizing conditions.

Example 17

Infra-Red Spectroscopy

The samples containing partially decomposed organic complex derived from Ru-triethanolamine and Ru-arginine were also analyzed using infrared spectroscopy. Approximately 25 mg of the materials of Example 7, $_{(TEA,\ calc\ 300°\ C.)}$, Example 12 $_{(no\ organic,\ dry\ 100°\ C.)}$ and Example 14 $_{(L\text{-}arginine,\ calc\ 250\ C)}$ were separately formed into 13 mm pellets and loaded into an IR spectrometer operating in transmission mode. The samples were heated in vacuum to 150° C. before the spectra were obtained.

Figure 4:
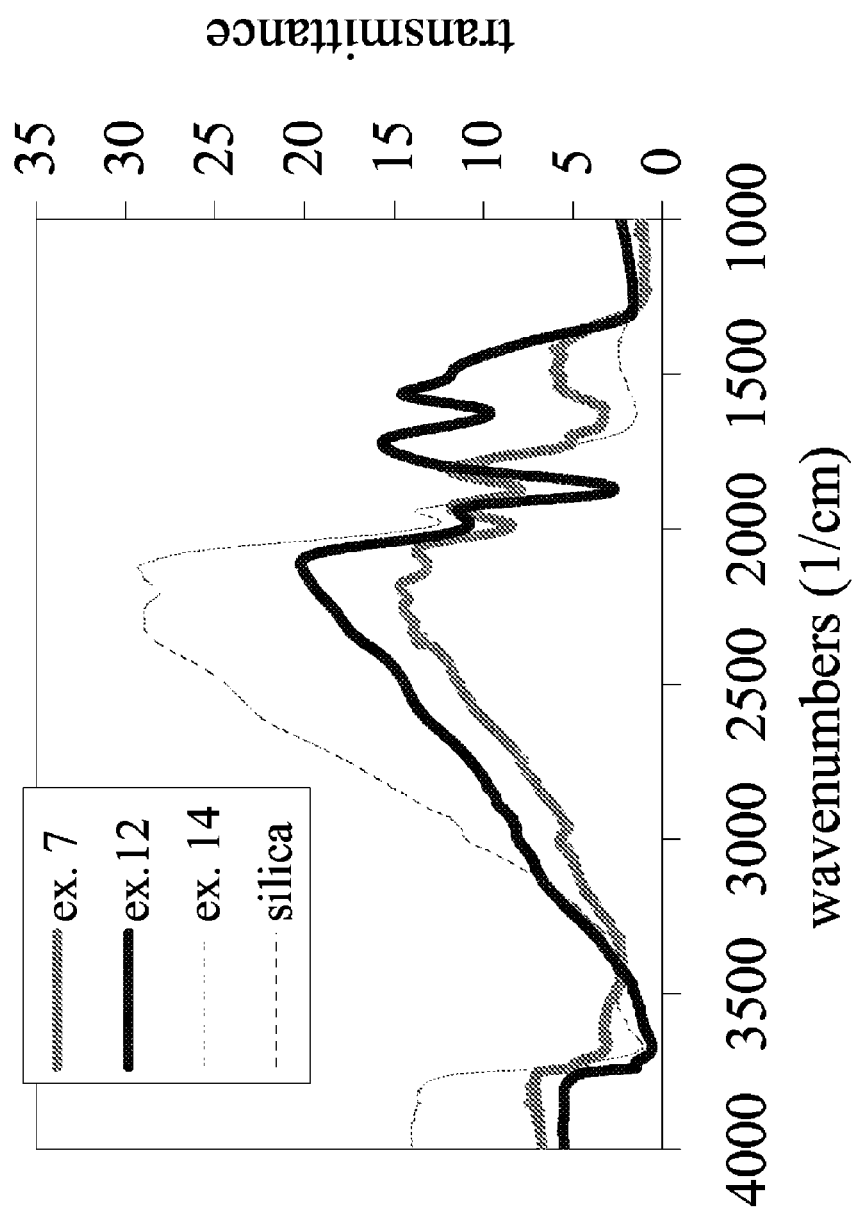
FIG. 4 shows the transmission infra-red spectra of silica and Examples 7, 9 and 14.

The data are shown in FIG. 4. The data shows the plot of transmittance vs. wave number of the IR radiation. The transmittance decreases where the catalyst absorbs infrared radiation due to a characteristic stretching of a molecular species. The peaks between 1500 and 2000 $cm^{-1}$ are primarily silica stretching bands. The presence of absorption features around 2100-2200 $cm^{-1}$, present on samples from Examples 7 and 14 are reported to be features of complexed carbon nitrogen species such as nitriles and isonitriles (see: Infrared and Raman Spectra of Inorganic and Coordination Compounds, by K. Nakamoto, John Wiley publishers, 3rd edition, 1978; ISBN: 0-471-62979-0 pages 267-269). The peaks are absent on the starting silica as well as on the sample prepared by aqueous impregnation of the ruthenium complex with no amino alcohol or amino acids present. Consequently these peaks are an indication of the remnant of the starting Ru-triethanolamine and Ru-arginine complexes present after partial decomposition of the organic complex.

Example 18

Thermogravimetric Analysis

Figure 5:
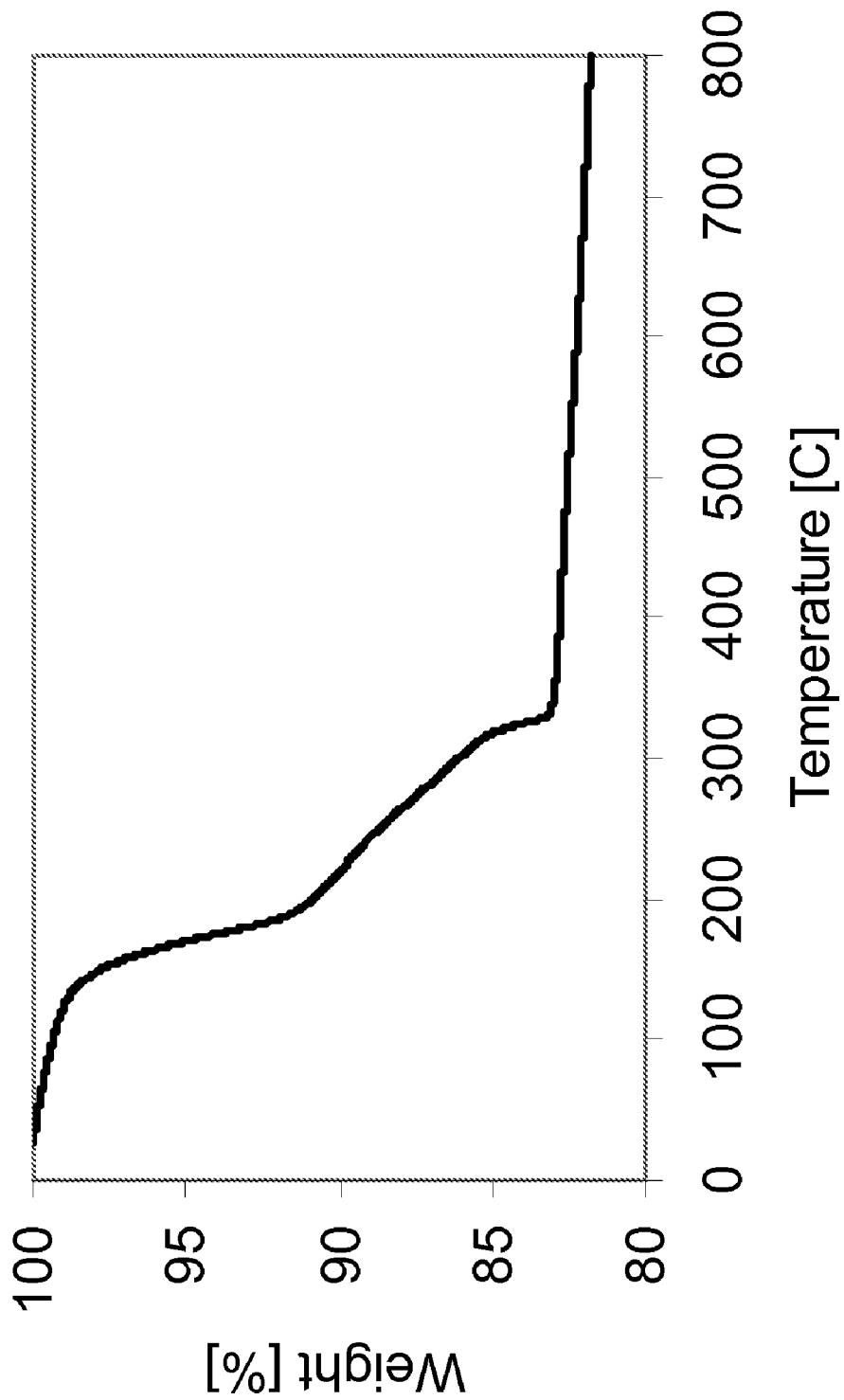
FIG. 5 shows an air treatment TGA plot for a supported metal catalyst (0.5 wt % Ru/SiO$_2$) prepared using impregnation of the metal with triethanolamine and drying at 100° C.

FIG. 5 shows the air treatment TGA plot for a catalyst sample (0.5 wt % Ru on $SiO_2$), which had been prepared with triethanolamine as the organic compound and dried at 100° C. prior to analysis. The TGA plot shows weight loss at temperatures below 300° C. due to loss of water and partial oxidation of the complex with triethanolamine. In addition there is a further weight loss at approximately 325° C., which is believed to be due to the complete oxidation of the organic complex.

Figure 6:
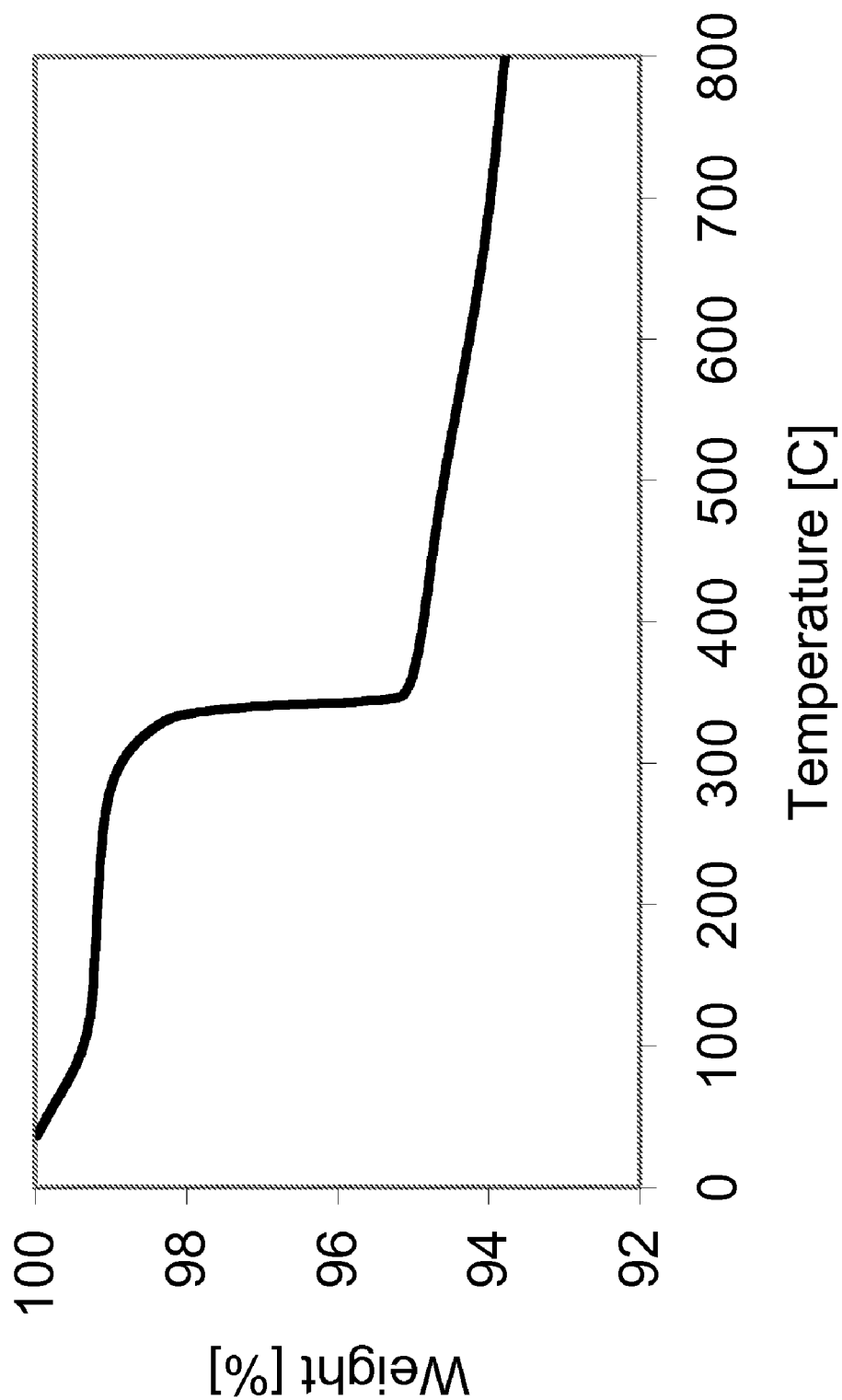
FIG. 6 shows an air treatment TGA plot for a supported metal catalyst (0.5 wt % Ru/SiO$_2$) prepared using impregnation of the metal with triethanolamine and calcination at 300° C.

FIG. 6 shows the air treatment TGA plot for a similar catalyst to that used in FIG. 1 (0.5 wt % Ru on $SiO_2$), which had previously been calcined at 300° C. Clearly there is an insignificant weight loss below 300° C.; this is due to the fact that any material on the supported catalyst that would have been removed below this temperature has been removed by the calcination. The majority of the weight loss in the sample is due to the partially decomposed organic complex, which is oxidized at approximately 325° C. This results shows that that calcination below the decomposition temperature is necessary to form the partially decomposed organic complex.

Figure 7:
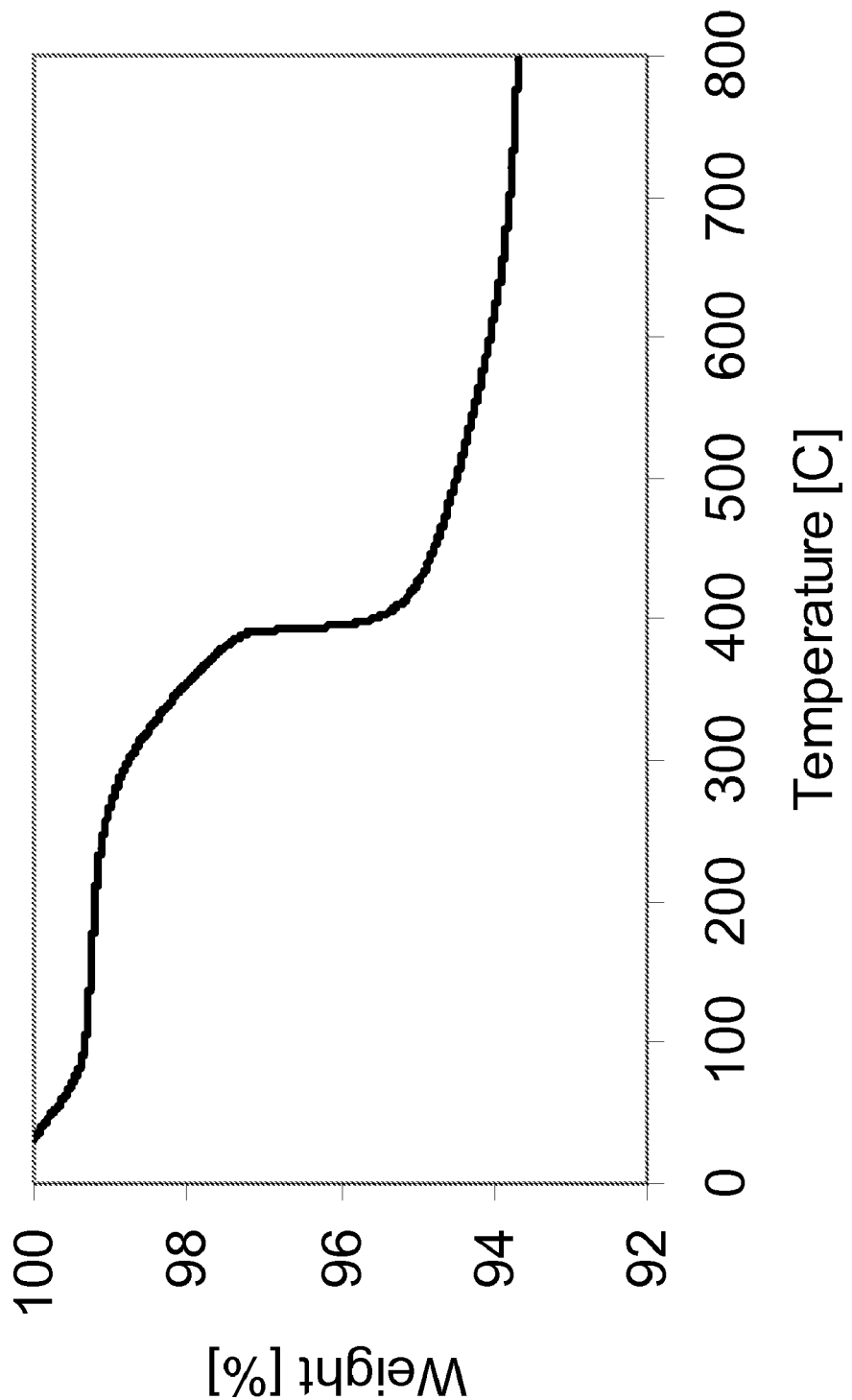
FIG. 7 shows a hydrogen treatment TGA plot for a supported metal catalyst (0.5 wt % Ru/SiO$_2$) prepared using impregnation of the metal with triethanolamine and calcination at 300° C.

FIG. 7 shows the hydrogen treatment TGA for the catalyst sample (0.5 wt % Ru on $SiO_2$), which had previously been calcined at 300° C. This TGA analysis shows that the partially oxidised organic complex is fully decomposed under the hydrogen treatment conditions at a higher temperature (~400° C.) than under calcination conditions.

Example 19

Preparation of 20% Ni/Al$_2$O$_3$ Conventional Preparation 20 grams of reforming grade gamma Al$_2$O$_3$ with a surface area of 190 m 2/g, was impregnated by incipient wetness with 12 cc of an aqueous impregnation solution containing 24.8 g of nickel nitrate hexahydrate. After being dried at 120° C., the sample was calcined at 350° C. for four hours.

Example 20

Preparation of 20% Ni/Al$_2$O$_3$ with DMEA Post-Treat on Dried Impregnate 20 grams of reforming grade gamma Al$_2$O$_3$ with a surface area of 190 m 2/g, was impregnated by incipient wetness with 12 cc of an aqueous impregnation solution containing 24.8 g of nickel nitrate hexahydrate. After being dried at 120° C., the sample was re-impregnated to incipient wetness with a 10.6 cc of an aqueous solution containing 7.6 grams of N,N-dimethylethanolamine. The sample was then dried at 120° C. overnight and then calcined at 350° C. for 4 hours. Under these conditions the organic complex was fully decomposed.

The dispersions of Ni the catalysts of Examples 19 and 20 was determined via a hydrogen chemisorption technique. The results are provided in Table 7. These results show a dramatic increase in Ni dispersion when the NI is deposited using the process of the present invention.

TABLE 1

| Example No | Catalyst | H$_2$ Activation | Metal Deposition | Weight DINP (g) | Weight Catalyst (g) | Temp (° C.) | Pressure (psig) | Time (h) | Conversion (%) | Lights (%) |
|---|---|---|---|---|---|---|---|---|---|---|
| 4 (a) | 0.5 wt % Ru MCM-41 | Ex 3 (a) | Ex 2 (a) | 137.4 | 6.87 | 120° C. | 3000 | 3 | 99.9 | 0.35 |
| 4 (b) | 0.5 wt % Ru MCM-41 | Ex 3 (a) | Ex 2 (a) | 118.2 | 5.91 | 80° C. | 3000 | 3 | 73.6 | 0.32 |
| 4 (c) (comp) | 0.5 wt % Ru MCM-41 | Ex 3 (a) | Ex 2 (b) (Comp) | 138.4 | 6.92 | 80° C. | 3000 | 3 | 37.9 | 0.16 |
| 4 (d) | 0.5 wt % Ru MCM-41 | Ex 3 (b) | Ex 2 (a) | 194.5 | 10 | 120° C. | 840 | 7.5 | 99.6 | 0.44 |
| 4 (e) (Comp) | 0.5 wt % Ru MCM-41 | Ex 3 (b) | Ex 2 (b) (Comp) | 190.5 | 10 | 120° C. | 840 | 7.5 | 93.7 | 1.22 |

Comp = comparative example

TABLE 2

| Sample of 0.5% Ru Supported on SiO$_2$ | Reduction temperature | % dispersion (combined) | % dispersion (weak) | % dispersion (strong) |
|---|---|---|---|---|
| Example 7 Ru-TEA/ 300° C. | 250 | 0 | 0 | 0.0 |
| | 325 | 0 | 0 | 0.0 |
| | 400 | 63.1 | 28.9 | 34.1 |
| | 400 | 66.4 | 29.7 | 36.7 |
| | 400 | 65.8 | 28.6 | 37.3 |
| | 400 | 65.8 | 29.0 | 36.9 |
| Example 8 Ru-TEA/ 400° C. | 250 | 16.18 | 7 | 9.2 |
| | 325 | 9.46 | 3.97 | 5.5 |
| | 400 | 8.69 | 1.67 | 7.0 |
| | 400 | 6.66 | 0 | 6.7 |

TABLE 3

| Sample of 0.5% Ru Supported on SiO$_2$ | Reduction temperature | % dispersion (combined) | % dispersion (weak) | % dispersion (strong) |
|---|---|---|---|---|
| Example 10 Ru/TEA/ 275° C. air | 250 | 0 | 0 | 0.0 |
| | 325 | 0 | 0 | 0.0 |
| | 400 | 57.6 | 29.9 | 27.7 |
| | 400 | 55.3 | 31.7 | 23.6 |
| Example 11 Ru/TEA/ 400° C. N$_2$ | 250 | 0 | 0 | 0.0 |
| | 325 | 0 | 0 | 0.0 |
| | 400 | 52.8 | 25.9 | 26.9 |
| | 400 | 60.8 | 30.6 | 30.2 |
| | 400 | 64.6 | 31.4 | 33.2 |
| | 400 | 64.7 | 31.5 | 33.2 |

TABLE 4

| Sample of 0.5% Ru Supported on SiO$_2$ | Reduction temperature | % dispersion (combined) | % dispersion (weak) | % dispersion (strong) |
|---|---|---|---|---|
| Example 7 Ru-TEA/ 300° C. | 250 | 0 | 0 | 0.0 |
| | 325 | 0 | 0 | 0.0 |
| | 400 | 63.1 | 28.9 | 34.1 |
| | 400 | 66.4 | 29.7 | 36.7 |
| | 400 | 65.8 | 28.6 | 37.3 |
| | 400 | 65.8 | 29.0 | 36.9 |
| Example 12 Ru-aq/ 100° C. | 150 | 77.77 | 40.87 | 36.9 |
| | 200 | 72.68 | 38.24 | 34.4 |
| | 250 | 66.54 | 36.51 | 30.0 |
| | 325 | 53.99 | 32.64 | 21.4 |
| | 400 | 45.98 | 27.67 | 18.3 |
| | 400 | 43.65 | 27.2 | 16.5 |
| | 400 | 42.64 | 25.84 | 16.8 |
| Example 13 Ru-aq/ 300° C. | 250 | 1.22 | 0 | 1.2 |
| | 325 | 0.38 | 0 | 0.4 |
| | 400 | 0.23 | 0 | 0.2 |

TABLE 5

| Sample of 0.5% Ru Supported on SiO$_2$ | Reduction temperature | % dispersion (combined) | % dispersion (weak) | % dispersion (strong) |
|---|---|---|---|---|
| Example 7 | 250 | 0 | 0 | 0.0 |
| Ru-TEA/ | 325 | 0 | 0 | 0.0 |
| 300° C. | 400 | 63.1 | 28.9 | 34.1 |
|  | 400 | 66.4 | 29.7 | 36.7 |
|  | 400 | 65.8 | 28.6 | 37.3 |
|  | 400 | 65.8 | 29.0 | 36.9 |
| Example 14 | 250 | 0 | 0 | 0.0 |
| Ru-arginine/ | 325 | 0 | 0 | 0.0 |
| 250° C. | 400 | 65.09 | 33.4 | 31.7 |
|  | 400 | 68.91 | 34.42 | 34.5 |

TABLE 6

| Sample of 0.5% Ru Supported on SiO$_2$ | Reduction temperature | % dispersion (combined) | % dispersion (weak) | % dispersion (strong) |
|---|---|---|---|---|
| Example 9 | 250 | 0 | 0 | 0.0 |
| Ru/TEA/ | 400 | 48.87 | 30.02 | 18.9 |
| dry 100 C. air | 400 | 49.79 | 29.3 | 20.5 |
|  | 400 | 49.86 | 30.55 | 19.3 |
| Example 10 | 250 | 0 | 0 | 0.0 |
| Ru/TEA/ | 325 | 0 | 0 | 0.0 |
| 275° C. air | 400 | 57.6 | 29.9 | 27.7 |
|  | 400 | 55.3 | 31.7 | 23.6 |

TABLE 7

| Sample Ni/Al$_2$O$_3$ | Treatment | Hydrogen chemisorption H/Ni in % |
|---|---|---|
| Example 19 | No post-treat nor additions to impregnation solution | 8.3 |
| Example 20 | N,N dimethylethanolamine post-treat dried impregnate/oxidize | 11.6 |

What is claimed is:

1. A process comprising:
   (a) contacting one or more aldehydes, ketones, carboxylic acids, carboxylic acid esters, carboxylic acid halides, and carboxylic acid anhydrides or a mixture of one or more aldehydes, ketones, carboxylic acids, carboxylic acid esters, carboxylic acid halides, and carboxylic acid anhydrides with a source of hydrogen in the presence of a catalyst comprising one or more catalytically active metal sites located on a catalyst support, under hydrogenation conditions, whereby at least one of said one or more aldehydes, ketones, carboxylic acids, carboxylic acid esters, carboxylic acid halides, and carboxylic acid anhydrides or mixture of one or more aldehydes, ketones, carboxylic acids, carboxylic acid esters, carboxylic acid halides, and carboxylic acid anhydrides is hydrogenated to provide a product;
   (b) recovering said product;
   wherein at least one of said catalytically active metal sites has been obtained via the partial decomposition on said catalyst support of a complex of a Transition Group VIII metal and a compound selected from the group consisting of (i) amino acids and (ii) aliphatic amines having one or more hydroxyl groups, partial decomposition having been carried out such that new vibration bands appear in the infra red spectrum of the complex at between 2100-2200 cm$^{-1}$ and (a) having been carried out in the presence of hydrogen or (b) being followed by treatment with hydrogen.

2. The process of claim 1, wherein said contacting in step (a) is carried out at a pressure of 25 to 300 bar.

3. The process of claim 1, wherein said contacting in step (a) is carried out at a pressure of 50 to 220 bar.

4. The process of claim 1, wherein the total metal dispersion of the hydrogenation catalyst is 45% or more and the metal dispersion relating to a strongly chemisorbed component of the total metal dispersion is 20% or greater.

5. The process of claim 1, wherein said decomposition is undertaken under hydrogen.

6. The process of claim 1, wherein after decomposition the partially or fully decomposed organic complex is treated with a source of hydrogen.

7. The process of claim 1, wherein said decomposition is undertaken via calcination, and said calcination temperature is less than the temperature, as determined by thermogravimetric analysis in air, at which total weight loss of the organic complex occurs.

8. The process of claim 7, wherein said calcination temperature is between 200° C. and the temperature at which total weight loss of the organic complex occurs.

9. The process of claim 1, wherein at least one of said support materials is one or more ordered mesoporous materials.

10. The process of claim 1, wherein at least one of said support materials is selected from the group consisting of at least one of silica, optionally, amorphous silica, MCM-41, MCM-48, and MCM-50.

11. The process of claim 1, wherein said Group VIII metal is selected from the group consisting of platinum, rhodium, palladium, cobalt, nickel, ruthenium, and a mixture of two or more thereof.

12. The process of claim 1, wherein the carboxylic acid esters are $C_1$- to $C_{10}$-alkyl esters or $C_1$- to $C_{20}$- alkyl esters.

13. The process of claim 1, wherein the carboxylic acid esters are derived from carboxylic acids selected from the group consisting of formic acid, acetic acid, propanoic acid, butanoic acid, iso-butanoic acid, n-valeric acid, pivalic acid, caproic acid, heptanoic acid, octanoic acid, decanoic acid, lauric acid, myristic acid, palmitic acid, stearic acid, acrylic acid, methacrylic acid, oleic acid, elaidic acid, linoleic acid, linolenic acid, cyclohexane carboxylic acid, benzoic acid, phenylacetic acid, o-, m-, p-toluylic acid, o-, p-chlorobenzoic acid, o-, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid, trimellitic acid, trimesic acid, pyromellitic acid, hemimellitic acid, and mixtures of two or more thereof.

14. The process of claim 1, wherein the carboxylic acid esters are alkyl terephthalates.

15. The process of claim 14, wherein the alkyl terephthalates are selected from the group consisting of at least one of monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate, dicyclohexyl terephthalate, and mixtures of one or more thereof.

16. The process of claim 1, wherein the carboxylic acid esters are alkyl phthalates.

17. The process of claim 16, wherein the alkyl phthalates are selected from the group consisting of at least one of monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, di-isoundecyl phthalate, diisododecyl phthalate, di-n-octadecyl phthalate, diisooctadecyl phthalate, di-n-eicosyl phthalate, monocyclohexyl phthalate, dicyclohexyl phthalate; alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate, dicyclohexyl isophthalate, and mixtures of one or more thereof.

18. The process of claim 1, wherein the carboxylic acid esters are alkyl trimellitates.

19. The process of claim 1, wherein the carboxylic acid esters are selected from the group consisting of at least one of di(isopentyl) phthalate; di(isoheptyl) phthalate; di(isononyl) phthalate; di(isononyl)phthalate which is based on n-butene; cyclohexane-1,2-dicarboxylic acid di(isononyl) ester; di(isononyl)phthalate which is based on isobutene; a 1,2-di-$C_9$-ester of cyclohexanedicarboxylic acid; di(nonyl)phthalate; di(isodecyl)phthalate; 1,2-$C_{7-11}$-ester of cyclohexanedicarboxylic acid; phthalic acid ester; 1,2-di-$C_{7-11}$-ester of cyclohexanedicarboxylic acid; di-$C_{7-11}$-phthalates; 1,2-di-$C_{9-11}$-ester of cyclohexanedicarboxylic acid;

a di-$C_{9-11}$-phthalate; a 1,2-di(isodecyl) cyclohexanedicarboxylic acid ester; di(isodecyl)phthalate, consisting essentially of di-(2-propylheptyl)phthalate; 1,2-di-$C_{7-9}$-cyclohexanedicarboxylic acid ester; di-$C_{7-9}$-alkylphthalate; di-$C_7$-alkylphthalate; and di-$C_9$-alkylphthalate; optionally, in the esters unpurified state to include one or more of the starting materials of the esters, and mixtures thereof.

20. The process of claim 1, wherein the carboxylic acid esters are selected from the group consisting of at least one of a $C_{5-7}$, $C_9$, $C_{10}$, $C_{7-11}$, $C_{9-11}$, $C_{7-9}$ esters, and mixtures thereof.

21. The process of claim 1, wherein the process further comprises, optionally:
  (a) activating the catalyst by contacting the catalyst with a gas stream comprising hydrogen at a temperature from 30 to 600° C.;
  (b) carrying out the process at a temperature from 50 to 250° C.;
  (c) carrying out the process continuously or batchwise;
  (d) carrying out the process in the presence or absence of a solvent or a diluent; and
  (e) any combination of the above (a)-(d).

22. The process of claim 21, wherein in (b) carrying out the process is at a temperature from 70 to 220° C. and/or wherein in (d) the solvent or the diluent is present and comprises water, an ether, an alcohol, an ester, optionally, a recycled intermediate ester feed, and mixtures thereof.

* * * * *